United States Patent [19]
Inaoka et al.

[11] Patent Number: 6,156,554
[45] Date of Patent: *Dec. 5, 2000

[54] HEAT-STABLE PROLYLENDOPEPTIDASE

[75] Inventors: Tetsuya Inaoka, Takatsuki; Toyomi Ohkuma-Soyejima, Nishinomiya; Toshio Kokubo, Sanda, all of Japan

[73] Assignee: Ciba Geigy Japan Limited, Hyogo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/750,816

[22] PCT Filed: Jun. 16, 1995

[86] PCT No.: PCT/IB95/00489

§ 371 Date: Jan. 8, 1997

§ 102(e) Date: Jan. 8, 1997

[87] PCT Pub. No.: WO96/00293

PCT Pub. Date: Jan. 4, 1996

[30] Foreign Application Priority Data

Jun. 23, 1994 [EP] European Pat. Off. .............. 94810377

[51] Int. Cl.[7] .............................. C12N 9/48; C12N 1/20; C12P 19/34; C07H 21/04
[52] U.S. Cl. .................... 435/212; 435/91.1; 435/252.3; 435/254.11; 435/320.1; 435/325; 536/23.2
[58] Field of Search ................. 435/212, 320.1, 435/325, 252.3, 254.11, 91.1; 536/23.2

[56] References Cited

U.S. PATENT DOCUMENTS 5,521,081  5/1996  Inaoka et al. ........................... 435/212

FOREIGN PATENT DOCUMENTS 516200   12/1992  European Pat. Off. .
0 524 906  1/1993  European Pat. Off. .

OTHER PUBLICATIONS

Luckow et al., Bio/Technology 6:47–55, 1988.
Habibi–Najafi et al., J. Dairy Sci. 77:385–392, 1994.
Krieg et al., Appl. Microbiol. Biotechnol. 42:844–852, 1995.
B. Cullen, *Methods in Enzymology*, 152, 696 (1987).
D. Leung et al., *Technique*, 1(1), 11–14 (1989).

*Primary Examiner*—Robert A. Wax
*Attorney, Agent, or Firm*—David E. Wildman

[57] ABSTRACT

The present invention relates to the field of biotechnology and concerns heat-stable prolylendopeptidase, recombinant DNA coding for heat-stable prolylendopeptidase, and processes for the production of heat-stable prolylendopeptidase and of recombinant DNA coding therefor, a host transformed with said recombinant DNA and a process for the production of said transformed host.

15 Claims, 3 Drawing Sheets

HEAT-STABLE PROLYLENDOPEPTIDASE

The present invention relates to the field of biotechnology and concerns heat-stable prolylendopeptidase, recombinant DNA coding for heat-stable prolylendopeptidase, and processes for the production of heat-stable prolylendopeptidase and of recombinant DNA coding therefor, a host transformed with said recombinant DNA and a process for the production of said transformed host.

DESCRIPTION OF THE RELATED ART

Prolylendopeptidase was first found in human uterus as a specific endopeptidase which cleaves a peptide at the carboxyl-terminal side of a proline residue. The unique substrate selectivity of the enzyme drew much attention to the study of its physiological functions. An endopeptidase that shows the same substrate specificity as mammalian prolylendopeptidase was found also in a bacterium, *Flavobacterium meningosepticum*. This finding made prolylendopeptidase commercially available and enabled its use as a biochemical reagent for the specific cleavage of peptides. The preparation of prolylendopeptidase from *F. meningosepticum*, however, has the following two crucial drawbacks arising from the bacterium. The bacterium is pathogenic and it produces not only prolylendopeptidase but also significant amounts of other specific or non-specific peptidases. The commercial preparations are thus contaminated with significant amounts of trypsin and aminopeptidase, which in fact, severely diminishes the utility of the commercial products as specific biochemical reagent.

Prolylendopeptidase catalyzes selective hydrolytic cleavage of peptides at the C-terminal side of a proline residue under physiological conditions. The enzyme can also catalyze the coupling of peptide fragments by condensation or transpeptidation, depending on reaction conditions and substrates. In the production of pharmaceutically active peptides, prolylendopeptidase can thus be used to catalyze i) selective cleavage of precursor peptides in order to liberate the pharmaceutically active peptide, ii) in vitro modification of peptides including amidation of C-termini and iii) coupling of peptides. The term peptide used herein shall not indicate that only short peptides are meant but that the molecules in question are composed of amino acids linked via peptide bonds. Peptides may be short peptides, oligopeptides or polypeptides.

Of the three reactions mentioned above, the former two are especially important for downstream processing in production processes of the peptides with recombinant DNA technology. The recombinant peptides are often expressed in the form of a precursor or fusion protein, which is then subjected to in vitro processing for the conversion to active or mature forms. Prolylendopeptidase is for example useful for C-terminal amidation of biologically active peptides such as ACTH, cholecystokin, calcitonin, endorphin, insulin, LH-RH, oxytocin and vasopressin, or the like. The characteristic substrate specificity of prolylenopeptidase makes it very useful for the cleavage of the precursors at specific sites and the in vitro modification of peptides without side reactions that are often associated with non-specific peptidases.

However, prolylendopeptidase is quite susceptible to inhibition or inactivation by conditions usually applied in peptidase catalyzed reactions. It is susceptible to denaturing and/or solubilizing agents in buffers used for cleavage of precursor peptides or also to conditions commonly used in peptidase catalyzed coupling reactions in order to make the formation of coupling products favourable over hydrolysis, e.g. the presence of high concentrations of organic solvents such as 1,4-dioxane, DMF or DMSO, extremes of pH and/or high temperature. Therefore, it is desirable to improve the stability of prolylendopeptidase in order to make it more versatile as a catalyst for the industrial production of peptides.

SUMMARY OF THE INVENTION

It is an object of the present invention to provide prolylendopeptidases which are more heat-stable than the corresponding wild type enzymes. Such a prolylendopeptidase is hereinafter named "heat-stable prolylendopeptidase".

A heat-stable prolylendopeptidase is particularly useful for an industrial production process of peptides, because its superior stability prolongs the life of the enzyme in the catalytic reactions and thus improves a total turnover of the endopeptidase. It is useful as a stable and selective catalyst for production of the biologically active peptides that contain proline residues. In other words, a heat-stable prolylendopeptidase can be used in much lower ratio to the substrates than that of the wild-type enzyme, decreasing costs of the catalyst which is often a critical factor for commercial feasibility of the production process. The high heat-stability of heat-stable prolylendopeptidases of the invention also enables the use thereof under the severe conditions that improve efficiencies, yields or conversions of the catalytic reactions, e.g., higher reaction temperature, extreme pH or the presence of a high concentration of organic solvent. A heat-stable prolylendopeptidase created in the present invention is also more resistant to other forms of protein denaturation, i.e. to other physical stress than heat inactivation and more resistant to treatment with chemicals. Thus, it is more-stable than the corresponding wild type enzyme in solutions containing organic solvents, denaturing agents or extreme pH.

Another object is to provide a method for the generation of heat-stable prolylendopeptidase starting from DNA coding for a wild-type enzyme and a method for the improvement of heat-stability by a "molecular evolution" method comprising multiple cycles of mutagenization and screening.

A further object of the present invention is to provide recombinant DNA coding for heat-stable prolylendopeptidase, a process for the production of such recombinant DNA, a host transformed with such recombinant DNA, and a process for the production of a heat-stable prolylendopeptidase by means of a transformed host.

DETAILED DESCRIPTION OF THE INVENTION

Figure 1:
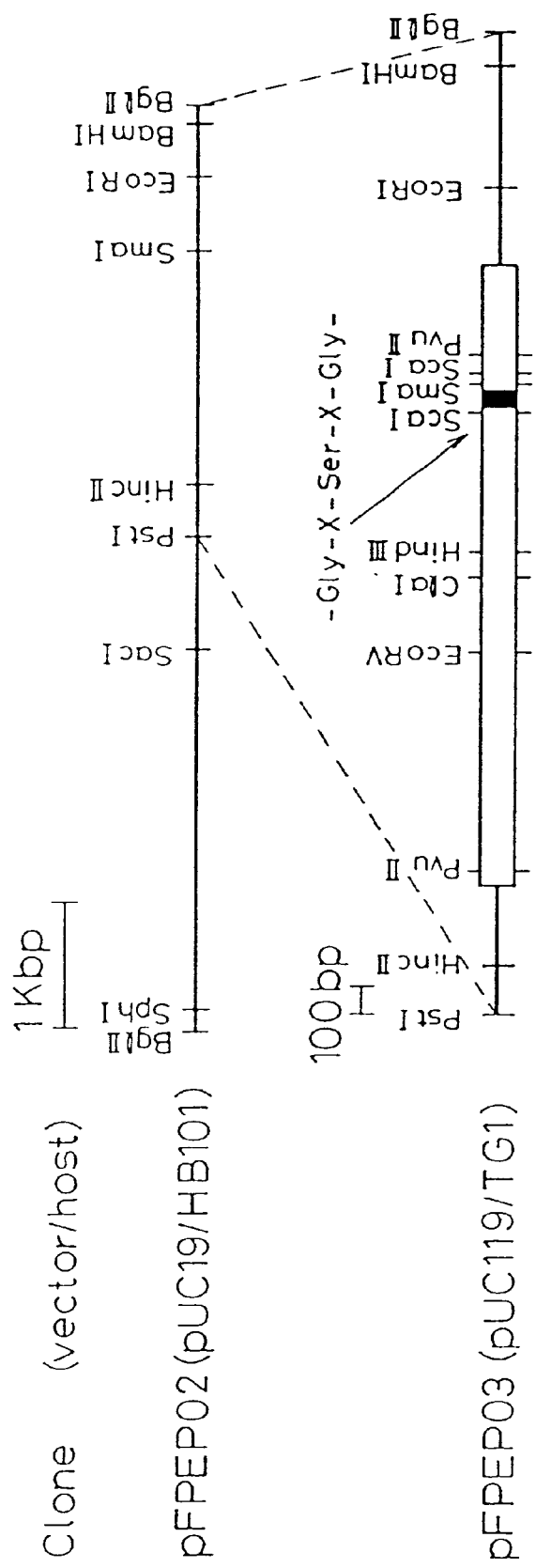
FIG. 1 represents restriction maps of the cloned inserts in pFPEPO2 and pFPEP03. The open box represents the open reading frame of the prolylendopeptidase gene and the solid box a consensus sequence of the catalytic site of serine protease.

Hereinafter, the term prolylendopeptidase is intended to include any prolylendopeptidase, i.e. any serine protease that catalyzes hydrolytic cleavage of peptides specifically at the carboxyl-terminus side of proline residues. The E.C. number of such a prolylendopeptidase is 3.4.21.26.

The preferred meaning of the term is a prolylendopeptidase derived from prokaryotes, preferably from *Flavobacterium spec.*, more preferably from *F. mennigosepticum*, most preferentially from *F. meningosepticum* strain IFO 12535 (ATCC 13253).

In order to obtain a heat-stable prolylendopeptidase of the present invention, a random mutagenesis of a wild-type prolylendopeptidase and subsequent screening for heat-stable prolylendopeptidases can be performed. For this purpose, for example, a wild-type prolylendopeptidase gene can be cloned and mutagenized. A key for a successful mutagenesis/screening approach is the preparation of good libraries of the mutated prolylendopeptidase genes and the use of an efficient screening method for the heat-stable prolylendopeptidase. For efficient screening for a clone producing a heat-stable prolylendopeptidase, it is essential to use an assay method that can identify a colony of the desired clone among thousands of colonies constituting a library of the mutants, namely a colony assay method. A colony assay for prolylendopeptidase, however, was not known. Therefore, in the present invention an example of a sensitive colony assay was developed which can be used for screening of heat-stable prolylendopeptidase.

Preparation of the Starting DNA for Mutagenization

There are DNA sequences known in the art which code for prolylendopeptidase and which can thus be used as starting material for the present invention. However, the skilled worker is not limited to the already known prolylendopeptidase sequences or to an available DNA preparation. It is also possible to prepare starting material for the present invention, i.e. DNA coding for prolylendopeptidase which is used for the preparation of a mutated DNA coding for a heat-stable prolylendopeptidase of the invention, from any cell or tissue comprising a prolylendopeptidase gene or, in the case of a eukaryotic cell or tissue, preferably from any cell or tissue expressing the prolylendopeptidase gene. In the case a eukaryotic DNA, preferably a mammalian DNA, for example from uterus or brain, e.g., of human or porcine origin, is chosen, the DNA is preferentially an intron-free cDNA. Preferred starting DNA for the present invention is derived from a bacterium belonging to the genus Flavobacterium, in particular *F. meningosepticum*, most preferentially *F. meningosepticum* strain IFO 12535 (ATCC 13253). The most preferred starting DNA is shown in SEQ ID NO. 1.

A starting DNA for the present invention can be prepared by different methods. Since DNA derived from a prokaryote does not include introns, a genomic DNA coding for a prolylendopeptidase-can be used as starting DNA if a prokaryotic cell is chosen as source. In this case, bacteria which contain a prolylendopeptidase gene, for example *F. meningosepticum*, can be homogenised and a whole genomic DNA can be extracted according to a conventional procedure. The extracted DNA can then be digested completely or partially with an appropriate restriction enzyme such as Bgl II, Eco RI, Hinc II, Hind III, Pst I or Bam MI. The digestion product can preferably be subjected to preparative electrophoresis with low-melting-point agarose gel to enrich DNA fractions of a certain length in order to enrich DNA fragments encoding prolylendopeptidase. Next, the DNA fragments may be cloned into a suitable cloning vector. The cloning vector may be derived from any vector useful in the art of genetic engineering, such as from viruses, phages, cosmids, plasmids or chromosomal DNA, for example derivatives of SV40, Herpes-viruses, Papilloma viruses, Retroviruses, Baculovirus, phage $\lambda$, e.g., NM989 or EMBL4, or phage M13, bacterial plasmids, e.g. pBR322, pUC18, pSF2124, pBR317 or pPLMu., or yeast plasmids, e.g. yeast 2$\mu$ plasmid, or also chromosomal DNA comprising an origin of replication or an autonomously replicating sequence (ARS). Preferably, the cloning vector is a bacterial vector such as pBR322, pUC18, pUC19, pUC118, pUC119, pKK 223-3 or the like.

Alternatively, a cDNA library may be prepared from a cell expressing prolylendopeptidase, e.g. from a bacterial cell such as preferably from a bacterium belonging to the genus *Flavobacterium*, in particular *F. meningosepticum*, most preferentially *F. meningosepticum* strain IFO 12535 (ATCC 13253), or from a eukaryotic cell or tissue, e.g. mammalian cell or tissue, which produces prolylendopeptidase, such as uterus or brain. For example, RNA is extracted from uterus or brain and enriched for mRNA according to a conventional procedure. Next, a cDNA library may be constructed according to a conventional procedure.

A variety of methods are known in the art for the incorporation of double-stranded cDNA or genomic DNA into an appropriate vector. For example, complementary homopolymer tracts may be added to the double-stranded DNA and the vector DNA by incubation in the presence of the corresponding deoxynucleoside triphosphates and an enzyme such as terminal deoxynucleotidyl transferase. The vector and double-stranded DNA are then joined by base pairing between the complementary homopolymeric tails and finally ligated by specific joining enzymes such as ligases. Other possibilities are the addition of synthetic linkers to the termini of the double-stranded DNA, or the incorporation of the double-stranded DNA into the vector by blunt- or staggered-end ligation.

Screening of the genomic DNA library or cDNA library is preferably achieved using a DNA hybridization probe. Suitable DNA probes are DNAs of known nucleotide sequence consisting of at least 17 nucleotides, for example synthetic DNAs, cDNAs derived from mRNA coding for prolylendopeptidase, or genomic DNA fragments comprising e.g. adjacent DNA sequences which are isolated from a natural source or from a genetically engineered microorganism.

To design synthetic DNA probes for screening the above-mentioned genomic DNA library or cDNA library, prolylendopeptidase for which a DNA coding region is to be cloned may be purified, and its partial amino acid sequence is determined according to a conventional procedure. Next, DNA sequences are designed on the basis of the partial amino acid sequence thus determined. Where an exact nucleotide sequence coding for the amino acid sequence is not known, a combination of nuceotide sequences which partially or totally cover possible nucleotide sequences present due to the degeneracy of genetic codon may be used. Alternatively, the third nucleotide in a codon may be replaced with inosine. Synthetic DNA probes can be synthesized according to known methods, for example by stepwise condensation using the solid phase phosphotriester, phosphite triester or phosphoramidite method, e.g., the condensation of dinucleotide coupling units by the phosphotriester method.

For hybridization, the DNA probes are labelled, e.g. radioactively labelled by the well known kinase reaction. The hybridization is performed according to known procedures, i.e., in buffer and salt solutions containing adjuncts, e.g. calcium chelators, viscosity regulating compounds, proteins, non-homologous DNA and the like, at temperatures favoring selective hybridization, e.g., between 0° C. and 80° C., for example between 25° C. and 50° C.

In order to obtain a preferred starting DNA of the present invention, a DNA library of *F. meningosepticum* can be used to transform an appropriate host such as *E. coli* cells, which are then plated and cultured on a solid medium to develop colonies, and positive clones can be selected by a colony hybridization method using the above-mentioned DNA probes. The transformation of appropriate host cells with the DNA library and the selection and multiplication of transformed host cells are well known in the art.

The nucleotide sequence of DNA selected as described above can be determined by methods known per se; for example, by the Maxam-Gilbert method using end-labelled DNA or by the dideoxy chain termination method of Sanger.

Once a nucleotide sequence coding for, or an amino acid sequence of, prolylendopeptidase is determined, DNA coding for the enzyme can also be prepared by methods leading directly the desired DNA such as conventional cloning or PCR procedures or e.g. an in vitro synthesis according to conventional methods. In an in vitro synthesis method suitably protected nucleotides are linked with one another e.g. by the phosphodiester method, the more efficient phosphotriester method, the phophite triester method or phosphoramidite method. Simplification of the synthesis of the oligonucleotides and polynucleotides is made possible by the solid phase method, in which the nucleotide chains are bound to a suitable polymer. The known synthesis techniques allow the preparation of polynucleotides up to 120 bases in length, in good yield, high purity and in a relatively short time. The actual double-stranded DNA is built up enzymatically from chemically prepared overlapping oligonucleotides from both DNA strands, which are held together in the correct arrangement by base-pairing and are then chemically linked by the enzyme DNA ligase. Another possibility comprises incubating overlapping single oligonucleotides from the two DNA strands in the presence of the four required deoxynucleoside triphosphates with a DNA polymerase, for example DNA polymerase I, the Klenow fragment of polymerase I or T4DNA polymerase, or with AMV (avian myeloblastosis virus) reverse transcriptase. The two oligonucleotides are thereby held together in the correct arrangement by base-pairing and are supplemented with the required nucleotides by the enzyme to give a complete double-stranded DNA.

Mutagenization and Screening

In the present invention an expression plasmid comprising a prolylendopeptidase expression cassette is used for the generation of heat-stable prolylendopeptidase by random mutagenization. Moreover, as is explained hereinafter in more detail, the present invention also concerns a method comprising multiple cycles of mutagenization which can be used for the preparation of improved heat-stable prolylylendopeptidase. Accordingly, the present invention concerns a method for the preparation of a recombinant DNA molecule coding for heat-stable prolylendopeptidase, said method comprising (a) mutagenization of a starting DNA coding for a prolylendopeptidase, whereby the starting DNA may be coding for a wild-type prolylendopeptidase or, if a second or further cycle of mutagenization is desired, a mutant DNA coding for a heat-stable "parent" prolylendopeptidase, (b) generation of a library of mutated DNA sequences obtained in (a), and (c) screening the library for a gene coding for a prolylendopeptidase with improved heat-stability, if compared to the corresponding wild-type enzyme or, after a second or further cycle of mutagenization, to the corresponding wild-type enzyme or optionally to the corresponding heat-stable "parent" prolylendopeptidase.

However, if the sequence of a heat-stable prolylendopeptidase is once known or if it is known, which amino acids positions can be mutated in order to improve heat stability, any method suitable for the generation of mutations or generation of a desired recombinant DNA sequence can be used. Therefore, the present invention is not limited only to recombinant DNA coding for heat-stable prolylendopeptidase obtained by the above-mentioned process based on random mutagenesis, but includes also DNA molecules of the invention obtained by another method.

If a prolylendopeptidase gene is desired to be randomly mutagenized, the conditions for mutagenization must be slightly adapted, for example as explained in the following, for each wild-type gene in order to obtain a suitable population of mutated clones in the library.

Usual conditions used for chemical mutagenesis are reported in "A General Method for Saturation Mutagenesis of Cloned DNA Fragments" [Myers R. M. et al., Science 229:242–247(1985)] as follows:

| Chemical mutagen | Concentration | Reaction time | Reaction temp. |
|---|---|---|---|
| Nitrous acid | 1 M[a] | 60 min | room temp. |
| Formic acid | 12 M | 10 min | room temp. |
| Hydrazine | 60% | 10 min | room temp. |

[a]1 M sodium nitrite in 250 mM sodium acetate, pH 4.3

The variable parameters of the conditions which have to be optimized for each gene or cDNA in order to obtain a suitable population of mutated clones in the library, are concentration of each chemical mutagen, reaction time and reaction temperature. In principle, the parameters should be adjusted so as to introduce a limited number of, i.e., a single or at most a few, base substitutions in the prolylendopeptidase gene. In the present invention it was found that the parameters could be adjusted conveniently by monitoring a) a number of transformed clones in the library of mutant prolylendopeptidase that is obtained from a certain, low amount (e.g. 10 ng to 1 $\mu$g) of the starting single-stranded DNA and b) the ratio of the number of the clones expressing the active enzyme to the total number of the transformants. The modified conditions adopted for the chemical mutagenesis of the prolylendopeptidase gene are as follows:

| Chemical mutagen | Concentration | Reaction time | Reaction temp. |
|---|---|---|---|
| Nitrous acid | 1 M[a] | 15–20 min | 20° C. |
| Formic acid | 3 M | 5–20 min | 20° C. |

-continued

| Chemical mutagen | Concentration | Reaction time | Reaction temp. |
|---|---|---|---|
| Hydrazine | 20% | 5–20 min | 20° C. |

[a]1 M sodium nitrite in 250 mM sodium acetate, pH 4.3

There are several factors that are known to influence the fidelity of DNA synthesis by *Thermus aquaticus* (Taq) DNA polymerase. For each factor, the normal conditions allowing the polymerase to function with high fidelity and a typical range of the condition known to reduce fidelity of DNA synthesis are as follows [taken from Leung et al., J. Methods Cell Mol. Bio. 1:11–15(1989) and Eckert et al., PCR (ed. McPherson et al.), 1991, pp. 225–244, IRL Press Oxford]:

| Factor influencing fidelity | Normal condition | Condition for reduced fidelity |
|---|---|---|
| Temperature | | 25–80° C. |
| pH | 8.3 | 5–8 |
| Addition of $Mn^{2+}$ | 0 µM | 500–1000 µM |
| Addition of DMSO | 0% | 10% |
| Higher conc. of $Mg^{2+}$ | 1.5 mM | 2–10 mM |
| [dATP]/[dNTP] | 1[b] | 0.02–0.2[c] |
| [dGTP]/[dNTP] | 1[b] | 5–10[d] |

[b]Conc. of dGTP, dTTP and dCTP are 0.2 mM
[c]Conc. of dGTP, dTTP and dCTP are 1 mM
[d]Conc. of dATP, dTTP and dCTF are 0.01 mM For example, conditions of chemical treatments for random mutagenesis are in the present invention optimized for the prolylendopeptidase gene cloned in the plasmid pUK-FPEP-b so as to introduce limited numbers of (a single or a few) base substitutions at random. Polymerase chain reaction (PCR) is also used as a method to induce base substitutions in the enzyme gene by the misincorporation of nucleotides. The effect of several factors decreasing the fidelity of the polymerase, such as the deoxyribonucleotide pool imbalance and addition of $MnCl_2$ or DMSO, is examined and reaction conditions are optimized for suitable frequencies of base substitutions.

In particular, the 2.3 kb EcoRI-PstI DNA fragment of pUK-FPEP-b encoding the wild-type prolylendopeptidase gene is amplified with a pair of 25 nucleotides primers, which are complementary to the regions immediately flanking the EcoRI and PstI sites.

To introduce a limited number of, i.e., a single or at most a few, base substitutions efficiently in the prolylendopeptidase gene, effects of several factors on the fidelity of the polymerase are examined. The factors investigated involve addition of $MnCl_2$ or DMSO, alteration on $MgCl_2$ concentration, and the deoxy nucleotide pool imbalance. A basic reaction mixture contains, 10 mM Tris HCl (pH 8.3), 50 mM KCl, 1.5 mM $MgCl_2$, 0.01% (w/v) bovine serum albumin, 0.2 mM each of four dNTP's, 10 ng/ml of the template plasmid, 1 µM each primers and 25 units/ml Taq polymerase. The modifications of the reaction condition decreasing the fidelity of the polymerase are as follows.

1) 50–100 µM of $MnCl_2$ can be added and the concentration of $MgCl_2$ can be increased to 5 mM.
2) 5–20% of DMSO can be added to the reaction mixture.
3) The concentration of $MgCl_2$ in the reaction mixture can be changed from 5 mM to 10 mM.
4) While the concentrations of dGTP, dTTP and dCTP are held constant at 1 mM, the concentration of dATP can be lowered from 0.2 mM to 0.1 mM in the presence of 5 mM $MgCl_2$.
5) While the concentrations of dATP, dCTP and dTTP are held constant at 0.1 mM, the concentration of dGTP can be varied from 0.5 mM to 1 mM in the presence of 1.5 –2 mM $MgCl_2$.

The PCR can be carried out according to conventional methods, e.g. by using Gene Amp™ PCR system 9600 (Perkin-Elmer). For example, the reactions can be carried out by melting the template DNA at 94° C. for 1 min and annealing with the primers at 50° C. for 1 min. Chain extension can for example be initiated at 70° C. for 4 min and a total of 25 cycles are performed and, after the last cycle, the polymerization at 70° C. can be extended for additional 7 min.

The mutated structure gene prepared by the chemical treatments or the PCR mutagenesis can then be excised and recloned into the native expression vector fragment according to conventional methods. With the mass of the reconstructed expression plasmid which typically consists of several tens of thousands of independent clones, *E. coli* is transformed to give a library of mutated prolylendopeptidase. The ratio of the number of the clones expressing the active enzyme to the total number of the transformants is used as an indication of frequencies of the base substitutions.

However, any other expression vector suitable for the preparation of a gene library which can be screened after the expression of the gene in question can be used for the generation of the gene library. Likewise, the method is not limited to the use of *E. coli* cells. Vectors and hosts which can be used are exemplified hereinbelow.

A colony assay method for the activity of prolylendopeptidase is used in order to develop the clones expressing heat-stable prolylendopeptidase. The assay comprises the steps (i) lysis of colonies on the filter, (ii) blocking of the filter and (iii) active staining of the enzyme. In a preferred embodiment, the filter is a nitrocellulose filter.

A method for the detection of prolylendopeptidase with Z-Gly-Pro-β-naphthylamide, Fast Garnet GBC and Triton X-100 has been known for a long time. In the present invention the assay method is modified and changed into a procedure of an active staining by removing the surfactant Triton X-100 from the assay mixture. By this staining method colonies producing active prolylendopeptidase are visualized as red spots on the filter.

A screening system for heat-stable prolylendopeptidase is built up by the combination of the colony assay and heat-treatment. The heat-treatment is performed after the lysis of the colonies on the filter and then the heat-treated filter is subjected to the active staining. Conditions of the heat-treatment are adjusted to allow selective staining of the colonies that produce mutants significantly more stable than the wild-type enzyme. The clones selectively stained in the first screening can be isolated and re-screened with heat-treatment at higher temperatures to be narrowed down to the most promising clone.

In the present invention clones are generated by the chemical mutagenesis/screening process and the PCR mutagenesis/screening process. Heat-stabilities of two heat-stable prolylendopeptidases, PEP-15 and PEP-227 obtained by the chemical and PCR mutagenesis, respectively, are quantitatively evaluated and compared with the wild-type enzyme in terms of first-order rate constants of heat inactivation at high temperatures. The evaluation has proven significant improvements in heat-stability of the mutant enzymes as is described in more detail in the Examples.

The whole nucleotide sequences of the structure genes of the heat-stable prolylendopeptidases PEP-15 and PEP-227 are determined and compared with that of the wild-type enzyme, revealing point mutations which lead to amino acid residue replacements responsible for the thermostability improvements.

For further improvement of heat-stability of prolylendopeptidase, a molecular evolutional approach can be taken: It has been clearly proven in the present invention that repeating the cycle of the mutagenesis and the screening is really effective to improve the thermostability of prolylendopeptidase. Thus a mutated gene coding for a heat-stable prolylendopeptidase can be isolated from the clone selected in the mutagenesis/screening process and it is again subjected to the mutagenesis to prepare the second generation library of mutated prolylendopeptidase. The second generation library is then screened for a clone producing a more heat-stable prolylendopeptidase. This mutagenesis/screening cycle can be repeated to improve stability of prolylendopeptidase as much as possible, mimicking the process of molecular evolution in vivo. The repeating mutagenesis/screening cycle allows selective accumulation of base substitutions (amino acid residue replacements) that synergistically and/or additively stabilize the enzyme molecule, and it is not necessary to determine the mutation (s) at each generation.

The repeating mutagenesis/screening cycle also permits accumulation of silent mutations (base substitutions) which does not alter the amino acid sequence. It is well recognized that a single base substitution in a codon does not result in every possible amino acid residue replacement because of the degeneracy of the genetic code. Since double or triple base substitutions in a single codon hardly take place at the same time under regular conditions of random mutagenesis, random mutagenesis is limited in the latitude replacements of every amino acid residue. The accumulation of silent mutations in the repeating mutagenesis/screening cycles, however, helps to extend this limit of amino acid replacements in further cycles of the mutagenesis/screening. Therefore, repeating the mutagenesis/screening cycle, i.e., a molecular evolution approach, is not only straightforward but also more thorough in the latitude of possible amino acid residue replacements.

More heat-stable prolylendopeptidases, PEP-361 and PEP-407 are isolated from the clones selected in the second and third cycles of the mutagenesis/screening, respectively. Their stabilities are quantitatively evaluated and compared with those of the wild-type enzyme and the heat-stable prolylendopeptidase of the first generation. It is confirmed that the heat-stabilities of the heat-stable prolylendopeptidases are constantly improved as the mutagenesis/screening cycles proceed, proving the efficacy of the molecular evolutional approach.

The determination of the DNA sequences of the mutated genes encoding PEP-361 and PEP-407 revealed the accumulation of base substitutions (and resulting amino acid residue replacements) as shown in Table 3 (Example 8). It is verified that the observed constant improvement in the heat-stability clearly correlates with collecting mutations in the enzyme molecule; a single or double mutations at each cycle. Besides the mutations leading to the amino acid residue replacements, accumulating silent mutations during the repeats of the mutagenesis/screening cycles are also demonstrated by the sequence analysis.

Like the starting DNA described above, a DNA molecule coding for a heat-stable prolylendopeptidase can also be prepared directly once the nucleotide or amino acid sequence is known, e.g. by the methods mentioned above for the production of the starting DNA.

Cloning Vectors and Expression Vectors

Hybrid vectors can be used for the propagation and multiplication of the starting DNA for mutagenesis, as well as for the cloning and preparation of the mutated prolylendopeptidase DNA and for the production of heat-stable prolylendopeptidase in a transformed host.

The hybrid vectors can be derived from any vector useful in the art of genetic engineering, such as from viruses, phages, cosmids, plasmids or chromosomal DNA, for example derivatives of SV40, Herpes-viruses, Papilloma viruses, Retroviruses, Baculovirus, phage λ, e.g. NM989 or EMBL4, or phage M13, bacterial plasmids, e.g. pBR322, pUC18, pSF2124, pBR317 or pPLMu., or yeast plasmids, e.g. yeast 2μ plasmid, or also chromosomal DNA comprising an origin of replication or an autonomously replicating sequence (ARS), or a defective virus, phage or plasmid in the presence of a helper virus, phage or plasmid allowing replication of said defective virus, phage or plasmid, e.g. M13(+)KS vector in presence of e.g. M13K07 helper phage. The Baculoviruses which can be used in the present invention are, for example, *Autographa californica* nuclear polyhedrosis virus (AcMNPV), *Trichoplusia ni* MNPV, Rachiplusia ou MNPV, *Galleria mellonella* MNPV, *Bombyx mori* nuclear polyhedrosis virus (BmNPV), and the like. A kit comprising a combination of an *Autographa californica* nuclear polyhedrosis virus and baculovirus transfer vectors pAc700, pAc701, pAc702, pVL1392 and pVL1393 is commercially available from Invitrogen.

Suitable vectors are those which are operable in the microbial host cell chosen for multiplying the hybrid vector or for the expression of heat-stable prolylendopeptidase. Suitable vectors thus contain a complete replicon and a marker gene, which renders possible the selection and identification of the microorganisms transformed by the expression plasmids by means of a phenotype feature. Vectors which by themselves do not fulfill all requirements for replication and/or expression but need helper plasmids which reconstitute missing functions may also be suitable Thus, hybrid vectors of the invention provide for replication of a desired prolylendopeptidase DNA in a suitable host, either as an extrachromosomal element or by integration in the host chromosome. Several possible vector systems are available for integration and expression of the cloned DNA of the invention. In principle, all vectors which replicate and/or comprise a recombinant gene which can be expressed in the chosen host are suitable. The vector is selected depending on the host cells envisaged for transformation. In general, such host cells may be prokaryotic or eukaryotic microorganisms such as bacteria, fungi such as yeasts or filamentous fungi, or cells of higher eukaryotic origin such as animal, for example mammalian or insect, cells. Suitable host cells will be discussed in detail hereinbelow. In principle, the hybrid vectors of the invention comprise a DNA encoding prolylendopeptidase, an origin of replication or an autonomously replicating sequence, optionally dominant marker sequences, and, optionally, additional restriction sites.

An origin of replication or an autonomously replicating sequence (a DNA element which confers autonomously replicating capabilities to extrachromosomal elements) is provided either by construction of the vector to include an exogeneous origin such as derived from Simian virus (SV40) or another viral source, or by the host cell chromosomal mechanisms.

A hybrid vector of the invention may contain selective markers depending on the host which is to be transformed, selected and cloned. Any marker gene can be used which facilitates the selection of transformants due to the phenotypic expression of the marker. Suitable markers are particularly genes from which a polypeptide can be expressed which provides resistance against compounds toxic to the receipt organism or which completes the enzyme system of a mutant lacking such an essential polypeptide, e.g. of an auxotrophic mutant. Suitable marker genes express, for example, antibiotic resistance, e.g. against tetracycline, ampicillin, or cycloheximide or provide for prototrophy in an auxotrophic mutant, for example in a yeast deficient in the ura3, leu2, his3 or trpl gene. It is also possible to employ as markers structural genes which are associated with an autonomously replicating segment providing that the host to be transformed is auxotrophic for the product expressed by the marker.

Hybrid vectors for the expression of a DNA coding for a heat-stable prolylendopeptidase have in general the same features as the hybrid vectors described hereinbefore for multiplication of DNA, and additionally comprise expression control sequences allowing the production and, optionally, the secretion of heat-stable prolylendopeptidase. Thus, hybrid expression vectors of the invention comprise a promoter region operably linked with a structural gene encoding heat-stable prolylendopeptidase and, optionally, if desired or needed, a DNA fragment encoding a leader or signal peptide, a transcriptional enhancer, a ribosomal binding site, a transcriptional terminator region and/or further regulatory sequences.

A wide variety of promoter sequences may be employed, depending on the nature of the host cell. Promoters that are strong and at the same time well regulated are the most useful. Sequences for the initiation of translation are for example Shine-Dalgarno sequences. Sequences necessary for the initiation and termination of transcription and for stabilizing the mRNA are commonly available from the noncoding 5'-regions and 3'-regions, respectively, of viral or eukaryotic cDNAs, e.g from the expression host.

Examples of suitable promoters are $\lambda P_L$, $\lambda P_R$, or $\lambda N$, $E.$ $coli$ lac, trp, tac, or lpp, yeast TRP1-, ADHI-, ADHII-, PHO3-, PHO5-, or glycolytic promoters such as the promoter of the enolase, glyceraldehyde-3-phosphate dehydrogenase, 3-phosphoglycerate kinase (PGK), hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase genes, or promoters derived from eukaryotic viruses, e.g. SV40, Rous sarcoma virus, adenovirus 2, bovine papilloma virus, papovavirus, cytomegalovirus or Baculovirus, e.g. *Autographa californica* nuclear polyhedrosis virus (AcMNPV), *Trichoplusia ni* MNPV, *Rachiplusia ou* MNPV, *Galleria mellonella* MNPV, derived promoters or mammalian cell derived promoters, e.g. of the actin, collagen, myosin, or β-globin gene. A preferred eukaryotic promoter is a polyhedrin gene promoter of a Baculovirus, preferentially of the *Autographa californica* nuclear polyhedrosis virus (AcMNPV). The eukaryotic promoters may be combined with enhancing sequences such as the yeast upstream activating sequences (UAS) or viral or cellular enhancers such as the cytomegalovirus IE enhancers, SV40 enhancer, immunoglobulin gene enhancer or others.

Enhancers useful for the expression are transcription-stimulating DNA sequences, e.g. derived from viruses such as Simian virus, Cytomegalovirus, polyoma virus, bovine papilloma virus or Moloney sarcoma virus, or of genomic origin. An enhancer sequence may also be derived from the extrachromosomal ribosomal DNA of *Physarum polycephalum*, or it may be the upstream activation site from the acid phosphatase PH05 gene, or the PH05, trp, PH05-GAPDH hybrid, or the like promoter.

Signal sequences which can be used in the present invention may be, for example, a presequence or secretory leader directing the secretion of the polypeptide, or the like. Signal sequences which can be used in the present invention are known in the literature. Another suitable signal sequence extends from amino acid 1 to 19 of the amino acid sequence depicted in the sequence listing under SEQ ID No.9.

A ribosomal binding site (Shine-Dalgarno Sequence) is either naturally linked to the promoter used or may be located on a short nucleotide sequence which may be covalently linked to the 5' end of the coding region for heat-stable prolylendopeptidase. Ribosomal binding sites are well known in the art.

A promoter chosen for the construction of a hybrid expression vector of the invention may be regulated by a regulatory protein and the production of heat-stable prolylendopeptidase in the transformed host cell then may be inducible or derepressible. The gene for the regulatory protein may be located either in the genome of the host strain, on an additional plasmid vector the host strain may be cotransformed with, or on the hybrid vector of the invention. The selection of a suitable gene for a regulatory protein depends on the promoter used. The conditions for the induction or derepression of the production of heat-stable prolylendopeptidase also depend on the promoter and on the regulatory protein. A regulatory protein which can be used in the present invention is, for example, a repressor protein, e.g. a product of the trpR, lacI, $\lambda$cro, or $\lambda$cI gene, or a temperature sensitive mutant thereof.

Preferred hybrid expression vectors of the invention are expression vectors suitable for the expression in *E. coli* of heat-stable prolylendopeptidase derivable from the amino acid sequence shown in SEQ ID No. 8, more preferably expression vectors comprising a signal sequence, preferably the signal sequence of the prolylendopeptidase gene shown under SEQ ID No. 1, operatively linked with the gene encoding the heat-stable prolylendopeptidase.

According to the above, the present invention concerns a recombinant DNA molecule comprising a DNA sequence coding for heat-stable prolylendopeptidase, which DNA sequence is derivable from a DNA sequence coding for a wild-type prolylendopeptidase, e.g. by a method comprising the steps (a) mutagenization of a starting DNA coding for a prolylendopeptidase, (b) generation of a library of mutated DNA sequences obtained in (a), and (c) screening the library for a gene coding for a prolylendopeptidase with improved heat-stability if compared to the corresponding wild-type enzyme.

A preferred recombinant DNA molecule is such comprising a DNA sequence coding for a preferred heat-stable prolylendopeptidase of the present invention.

Accordingly, a preferred recombinant DNA molecule comprises a DNA sequence coding for a heat-stable prolylendopeptidase derivable from a prolylendopeptidase of a prokaryote, preferably from *Flavobacterium spec.*, more preferably from *F. menigosepticum*, most preferentially from *F. meningosepticum* strain IFO 12535 (ATCC 13253).

More preferred is a recombinant DNA molecule comprising a DNA sequence coding for a heat-stable prolylendopeptidase which derivable from a prolylendopeptidase having the sequence with SEQ ID No. 8.

More preferred is a recombinant DNA molecule comprising a DNA sequence coding for a heat-stable prolylendopeptidase derivable from a DNA molecule having the sequence with SEQ ID No. 1.

Even more preferred is a recombinant DNA molecule comprising a DNA sequence coding for a heat-stable prolylendopeptidase selected from the group of heat-stable prolylendopeptidases having SEQ ID No. 8 with amino acid Glu in position 48 ("Glu48"), Phe51, Ala129, Gly633 and/or Glu477 replaced by another amino acid.

Even more preferred is a recombinant DNA molecule comprising a DNA sequence coding for a heat-stable prolylendopeptidase, which recombinant DNA molecule is selected from the group of recombinant DNA molecules having the sequence of nucleotides 317 to 2374 of SEQ ID No. 1 with the codons for amino acid Glu in position 48, Phe51, Ala129, Gly633 and/or Glu477 replaced by a codon coding for another amino acid.

More preferred is also a recombinant DNA molecule comprising a DNA sequence coding for a heat-stable prolylendopeptidase selected from the group of heat-stable prolylendopeptidases having SEQ ID No. 8 with amino acid Glu48 replaced by Gln, Phe51 replaced by Leu, Ala129 replaced by Thr, Gly633 replaced by Val and/or Glu477 replaced by Lys.

More preferred is also a recombinant DNA molecule comprising a DNA sequence coding for a heat-stable prolylendopeptidase selected from the group of DNA molecules having nucleotides 317 to 2374 of SEQ ID No. 1 with the codon coding for amino acid Glu48 replaced by a codon coding for Gln, the codon coding for Phe51 replaced by a codon coding for Leu, the codon coding for Ala129 replaced by a codon coding for Thr, the codon coding for Gly633 replaced by a codon coding for Val and/or the codon coding for Glu477 replaced by a codon coding for Lys.

Even more preferably the invention concerns a recombinant DNA molecule comprising a DNA sequence coding for a heat-stable prolylendopeptidase selected from the group of heat-stable prolylendopeptidases having SEQ ID No. 8 with amino acid (a) Glu48, (b) Glu48, Ala129 and Gly633, (c) Glu48, Ala129, Gly633 and Phe51, and (d) Glu477 replaced by another amino acid.

Even more preferably the invention concerns a recombinant DNA molecule comprising a DNA sequence coding for a heat-stable prolylendopeptidase selected from the group of DNA molecules having nucleotides 317 to 2374 of SEQ ID No. 1 with the codons coding for amino acid (a) Glu48, (b) Glu48, Ala129 and Gly633, (c) Glu48, Ala129, Gly633 and Phe51, and (d) Glu477 replaced by codons coding for another amino acid.

Even more preferred is also a recombinant DNA molecule comprising a DNA sequence coding for a heat-stable prolylendopeptidase selected from the group of heat-stable prolylendopeptidases having SEQ ID No. 8 with amino acids (a) Glu48 replaced by Gln (PEP-227), (b) Glu48 replaced by Gln, Ala129 replaced by Thr and Gly633 replaced by Val (PEP-361) (c) Glu48 replaced by Gln, Ala129 replaced by Thr, Gly633 replaced by Val and Phe51 replaced by Leu (PEP-407), and (d) Glu477 replaced by Lys (PEP-15).

Even more preferred is also a recombinant DNA molecule comprising a DNA sequence coding for a heat-stable prolylendopeptidase selected from the group of DNA molecules having nucleotides 317 to 2374 of SEQ ID No. 1 with (a) the codon coding for amino acid Glu48 replaced by a codon coding for amino acid Gln, (b) the codon coding for amino acid Glu48 replaced by a codon coding for amino acid Gln, the codon coding for amino acid Ala129 replaced by a codon coding for amino acid Thr and the codon coding for amino acid Gly633 replaced by a codon coding for amino acid Val (c) the codon coding for amino acid Glu48 replaced by a codon coding for amino acid Gln, the codon coding for amino acid Ala29 replaced by a codon coding for amino acid Thr, the codon coding for amino acid Gly633 replaced by a codon coding for amino acid Val and the codon coding for amino acid Phe51 replaced by a codon coding for amino acid Leu, and (d) the codon coding for amino acid Glu477 replaced by a codon coding for amino acid Lys.

Moreover, the invention preferably concerns also a recombinant DNA molecule comprising a DNA sequence coding for a heat-stable prolylendopeptidase selected from the group of DNA molecules having nucleotides 317 to 2374 of SEQ ID No. 1 with (a) the nucleic acid G in position 458 ("458 G") replaced by C, (b) 458 G replaced by C, 701 replaced by A, and 2214 G replaced by T (c) 458 G replaced by C, 701 (replaced by A, and 2214 G replaced by T, and 467 T replaced by C, and (d) 1745 G to A.

Even more preferred is a recombinant DNA molecule comprising a DNA sequence coding for a heat-stable prolylendopeptidase selected from the group of DNA molecules coding for a heat-stable prolylendopeptidase in pUK-FPEP-15, in pUK-FPEP-227, in pUK-FPEP-361, or in pUK-FPEP-407.

A recombinant DNA molecule according to the present invention may be an isolated DNA fragment coding for a heat-stable prolylendopeptidase according to the invention, e.g. such consisting only of the coding region or also such being prolonged by homologous or heterologous DNA sequences. A prolonged fragment may, for example, contain linker sequences, e.g. for cloning purposes, or may be linked to other fragments containing marker genes or functional elements for replication or gene expression. Such fragments can be used for transformation of host cells or as intermediates for the generation of cloning and/or expression vectors. A recombinant DNA molecule according to the present invention also includes hybrid vectors for the propagation and multiplication of a DNA sequence coding for a heat-stable prolylendopeptidase of the invention, and expression vectors for the expression thereof in a suitable transformed host.

Preferred expression vectors are those for the expression in a Baculovirus/insect cell expression system or in *E. coli*.

Most preferred are expression vectors pUK-FPEP-15, pUK-FPEP-227, pUK-FPEP-361, and pUK-FPEP407.

The present invention also concerns the preparation of a recombinant DNA molecule of the invention, preferably of a hybrid vector or of a hybrid expression vector of the invention.

Transformed Hosts and Preparation Thereof

The invention also concerns a transformed host cell for multiplicating a recombinant DNA molecule of the invention or particularly for the production of a heat-stable prolylendopeptidase, as well as a process for the preparation of such a transformed host cell.

Hosts mentioned herein can also be used for the multiplication of the starting DNA used for mutagenesis, and for the generation of a library of mutated prolylendopeptidase genes.

The transformed microbial host strains are cultured in a liquid medium containing sources of carbon and nitrogen which can be assimilated by the microbial cell, and inorganic salts, applying methods known in the art. The culture of the hosts is carried out in a conventional nutrient medium which may be supplemented with or deprived of chemical compounds allowing negative or positive selection of the transformants, i.e. such hosts containing the desired DNA molecule together with a selection marker, from the non-transformants, i.e. such hosts lacking the desired DNA molecule.

Any transformable hosts useful in the art may be used, e.g. bacteria, such as *E. coli*, fungi, such as *Saccharomyces cerevisiae, Kluyveromyces lactis*, or filamentous fungi, such as *Aspergillus Spec.*, e.g. *A. nidulans, A. oryzae, A. carbonarius, A. awamori* or *A. niger*. However, the use of suitable hosts which are devoid of or poor in restriction enzymes or modification enzymes may be advantageous. Examples of such hosts are bacteria, e.g. *Bacillus subtilis, Bacillus stearothermophilus*, Pseudomonas, Haemophilus, Streptococcus and others, and yeasts, for example *Saccharomyces cerevisiae*, and in particular strains of *Escherichia coli*, for example *E. coli* X1776, *E. coli* Y1090, *E. coli* W3110, *E. coli* HB101/LM1035, *E. coli* JA 221, *E. coli* DH5α, or preferentially *E. coli* DH5αF', JM109, MH1 or HB 101, or *E. coli* K12 strain. Further suitable hosts are cells of higher organisms, in particular established continuous human or animal cell lines, e.g. human embryonic lung fibroblasts L132, human malignant melanoma Bowes cells, HeLa cells, SV40 virus transformed kidney cells of African green monkey COS-7 or Chinese hamster ovary (CHO) cells. Other suitable host cells are established insect cell lines, for example, *Spodoptera frugiperda*, such as Sf21 or preferentially Sf9 (ATCC CRL171 1), *Mamestra brassicae, Bombyx mori* cell systems using *Bombyx mori* nuclear polyhedrosis virus (BmNPV) and the like.

The present invention also concerns the preparation of a host transformed with a recombinant DNA molecule of the invention. The preparation of such transformed hosts comprises the treatment of a desired suitable host cell under transforming conditions with a desired recombinant DNA molecule of the present invention, preferably a hybrid vector or hybrid expression vector of the invention, optionally together with a selection marker gene and optionally selecting the transformants. Transformation of microorganisms is carried out according to conventional methods as described in the literature.

Accordingly, the transformation procedure of *E. coli* cells includes, for example, $Ca^{2+}$ pretreatment of the cells so as to allow DNA uptake, and incubation with the hybrid vector. The subsequent selection of the transformed cells can be achieved, for example, by transferring the cells to a selective growth medium which allows separation of the transformed cells from the parent cells dependent on the nature of the marker sequence of the vector DNA. Preferably, a growth medium is used which does not allow growth of cells which do not contain the vector. The transformation of yeast comprises, for example, steps of enzymatic removal of the yeast cell wall by means of glucosidases, treatment of the obtained spheroplasts with the vector in the presence of polyethylene glycol and $Ca^{2+}$ ions, and regeneration of the cell wall by embedding the spheroplasts into agar. Preferably, the regeneration agar is prepared in a way to allow regeneration and selection of the transformed cells as described above at the same time.

Transformation of cells of higher eukaryotic origin, such as mammalian cell lines, is preferably achieved by transfection. Transfection is carried out by conventional techniques, such as calcium phosphate precipitation, microinjection, protoplast fusion, electroporation, i.e. introduction of DNA by a short electrical pulse which transiently increases the permeability of the cell membrane, or in the presence of helper compounds such as diethylaminoethyldextran, dimethyl sulfoxide, glycerol or polyethylene glycol, and the like. After the transfection procedure, transfected cells are identified and selected e.g. by cultivation in a selective medium chosen depending on the nature of the selection marker, for example standard culture media such as Dulbecco's modified Eagle medium (DMEM), minimum essential medium, RPMI 1640 medium and the like, containing e.g. the corresponding antibiotic.

The transformed host cells are cultured by methods, known in the art in a liquid medium containing assimilable sources of carbon, e.g. carbohydrates such as glucose or lactose, nitrogen, e.g. amino acids, peptides, proteins or their degradation products such as peptones, ammonium salts or the like, and inorganic salts, e.g. sulfates, phosphates and/or carbonates of sodium, potassium, magnesium and calcium. The medium furthermore contains, for example, growth-promoting substances, such as trace elements, for example iron, zinc, manganese and the like.

The medium is preferably so chosen as to exert a selection pressure and prevent the growth of cells which have not been transformed or have lost the hybrid vector. Thus, for example, an antibiotic is added to the medium if the hybrid vector contains an antibiotic resistance gene as marker. If, for instance, a host cell is used which is auxotrophic in an essential amino acid whereas the hybrid vector contains a gene coding for an enzyme which complements the host defect, a minimal medium deficient of the said amino acid is used to culture the transformed cells.

Cells of higher eukaryotic origin such as mammalian cells are grown under tissue culture conditions using commercially available media, for example Dulbecco's modified Eagle medium (DMEM), minimum essential medium, RPMI 1640 medium and the like as mentioned above, optionally supplemented with growth-promoting substances and/or mammalian sera. Techniques for cell cultivation under tissue culture condition are well known in the art and include homogeneous suspension culture, e.g. in an airlift reactor or in a continuous stirrer reactor, or immobilized or entrapped cell culture, e.g. in hollow fibers, microcapsules, on agarose microbeads, porous glass beads, ceramic cartridges, or other microcarriers.

Culturing is effected by processes which are known in the art. The culture conditions, such as temperature, pH value of the medium and fermentation time, are chosen so that a maximum expression level of the polypeptide or derivative of the invention is obtained. Thus, an *E. coli* or yeast strain is preferably cultured under aerobic conditions by submerged culture with shaking or stirring at a temperature of about 20° C. to 40° C., preferably at about 37° C., and a pH value of 4 to 8, preferably of about 7, for about 4 to 30 hours, preferably until maximum yields of the polypeptide or derivative of the invention are reached.

Heat-stable Prolylendopeptidase

Accordingly, the present invention concerns a heat-stable prolylendopeptidase obtainable by a process comprising the steps (a) mutagenization of a starting DNA coding for a prolylendopeptidase, (b) generation of a library of mutated DNA sequences obtained in (a), (c) screening the library for a gene coding for a prolylendopeptidase with improved heat-stability if compared to the corresponding wild-type enzyme, and (d) expression of the gene obtained under (c) and isolating the expression product.

A preferred heat-stable prolylendopeptidase is such derivable from a prolylendopeptidase of a prokaryote, preferably from *Flavobacterium spec.*, more preferably from *F. menigosepticum*, most preferentially from *F. meningosepticum* strain IFO 12535 (ATCC 13253).

More preferred is a heat-stable prolylendopeptidase derivable by random mutagenesis from a prolylendopeptidase having the sequence with SEQ ID No. 8.

It is shown in the present invention that changes in amino acid position 48, 51, 129, 477 and 633 of the sequence of SEQ ID No. 8 increase the heat-stability of the prolylendopeptidase. Accordingly, the invention concerns even more preferably a heat-stable prolylendopeptidase selected from the group of heat-stable prolylendopeptidases having SEQ ID No. 8 with amino acid Glu in position 48 ("Glu48"), Phe51, Ala129, Gly633 and/or Glu477 replaced by another amino acid.

More preferred is also a heat-stable prolylendopeptidase selected from the group of heat-stable prolylendopeptidases having SEQ ID No. 8 with amino acid Glu48 replaced by Gln, Phe51 replaced by Leu, Ala129 replaced by Thr, Gly633 replaced by Val and/or Glu477 replaced by Lys.

Even more preferably the invention concerns a heat-stable prolylendopeptidase selected from the group of heat-stable prolylendopeptidases having SEQ ID No. 8 with amino acid (a) Glu48, (b) Glu48, Ala129 and Gly633, (c) Glu48, Ala129, Gly633 and Phe51, and (d) Glu477 replaced by another amino acid.

Even more preferred is also a heat-stable prolylendopeptidase selected from the group of heat-stable prolylendopeptidases having SEQ ID No. 8 with amino acids (a) Glu48 replaced by Gln (PEP-227), (b) Glu48 replaced by Gln, Ala129 replaced by Thr and Gly633 replaced by Val (PEP-361) (c) Glu48 replaced by Gln, Ala129 replaced by Thr, Gly633 replaced by Val and Phe51 replaced by Leu (PEP-407), and (d) Glu477 replaced by Lys (PEP-15).

Production of Heat-stable Prolylendopeptidase

The present invention concerns also a method for the production of prolylendopeptidase.

For the expression of prolylendopeptidase, either prokaryotic or eukaryotic host cells may be used as indicated above, e.g. *E. coli* strains defective in protease genes, e.g. in the lon protease gene, and genes involved in the regulation of heat shock induced protein synthesis, e.g. in the htpR gene.

Preferably, prolylendopeptidase is produced in *E. coli*. In this case, to improve the expression, a 5'-terminal noncoding region of the cloned DNA is preferably removed while maintaining the full length of the coding region, preferably the coding region of a mature heat-stable prolylendopeptidase preferred above. The coding region is most preferably functionally linked with a signal sequence allowing the secretion of the heat-stable prolylendopeptidase. Moreover, the structural gene is functionally linked with a promoter region functional in *E. coli*, either homologous or preferably heterologous to the desired prolylendopeptidase coding region. The linkage is performed according to a conventional procedure, for example, using an appropriate restriction enzyme site or deletion by digesting with an exonuclease such as *E. coli* exonuclease III and successive blunting with a nuclease, e.g. mung-bean nuclease.

In a preferred embodiment of the invention, a genomic DNA having a linker sequence immediately upstream of a full length coding region for heat-stable prolylendopeptidase is linked with a heterologous promoter such as tac promoter in an expression vector, for example, a plasmid based on pUC119 plasmid. More preferably a coding region in the genomic DNA from *Flavobacterium meningosepticum* encodes a pro-form of a desired prolylendopeptidase of the invention, e.g. such consisting of a mature form of a heat-stable prolylendopeptidase and a signal peptide, for example amino acid residues 1 to 19 of the sequence shown under SEQ ID No. 9. When such a type of an expression plasmid is used to transform *E. coli* host, and the transformant is cultured, then heat-stable prolylendopeptidase is produced in *E. coli* cells and secreted into the periplasmic region. In the process of secretion the signal peptide is removed to give a mature form of the enzyme which is not incorporated in inclusion bodies, and therefore, the produced heat-stable prolylendopeptidase is easily recovered.

According to another embodiment of the present invention, a DNA coding for the present enzyme is inserted into a baculovirus transfer vector to construct a recombinant baculovirus transfer vector, and the recombinant baculovirus transfer vector is then co-transfected with a baculovirus DNA to insect cells to carry out a homologous recombination.

The baculovirus transfer vector is usually a plasmid containing a segment of baculovirus DNA, which segment comprises a gene not essential for the replication of baculovirus. The gene not essential for the replication of baculovirus is, for example, a polyhedrin gene comprising a polyhedrin structure gene and a promoter thereof. Such baculovirs transfer vectors known in the art are, for example, pAcYM1, pAc311, pAc360, pAc373, pAc380, pAc700, pAc701, pAc702, pVL1392, pVL1393.

Baculoviruses which can be used in the present invention are, for example, *Trichoplusia ni* MNPV, *Rachiplusia ou* MNPV, *Galleria mellonella* MNPV, and the like. Preferentially used is *Autographa californica* nuclear polyhedrosis virus (AcMNPV). A kit comprising a combination of an *Autographa californica* nuclear polyhedrosis virus and baculovirus transfer vectors pAc700, pAc701, pAc702, pVL1392 and pVL1393 is commercially available from Invitrogen Corp., San Diego, Calif., USA. Insect cells useful in the present invention are established insect cell lines, for example, *Spodoptera frugiperda*, such as Sf21 or preferentially Sf9 (ATCC CRL1711), but also *Mamestra brassicae* and the like. A *Bombyx mori* cell system using *Bombyx mori* nuclear polyhedrosis virus (BmNPV) can also be used in the present invention.

The homologous recombination can be carried out in accordance with a conventional procedure as described, for example, in "A Manual of Methods for Baculovirus Vectors and Insect Cell Culture Procedures, M. D. Summers et al., Texas Agricultural Experiment Station Bulletin No. 1555". The transfected insect cells can be cultured in accordance with a conventional procedure. Namely, the transfected insect cells may be cultured in any tissue culture medium in which insect cells can grow, such as Grace's or TC100 medium supplemented with mammalian serum, serum-free medium EX-CELL400, or the like, at a temperature of 20° C. to 30° C., preferably 27° C. to 28° C., for example 27° C., for 2 to 10 days, preferably 3 to 5 days.

The expressed prolylendopeptidase can be extracted from microbial cells such as *E. coli* cells or a supernatant of a cell culture by conventional methods, e.g., comprising homogenization of the cells, chromatography such as ion-exchange, hydrophobic or size-exclusion chromatography, precipitation, e.g., with ammonium sulfate or acid, preparative electrophoresis such as polyacrylamide gel electrophoresis or isoelectric focussing, and the like. Particularly, heat-stable prolylendopeptidase derivable from *Flavobacterium meningosepticum* wild-type enzyme, which is expressed in *E. coli*, is easily and selectively extracted from the cells with an osmotic shock method if the enzyme is secreted to the periplasmic region. The obtained crude enzyme can be further purified with usual methods, e.g. comprising chromatography such as ion-exchange, hydrophobic or size-exclusion chromatography, preparative electrophoresis such as polyacrylamide gel electrophoresis, or isoelectric focussing, and the like.

Production of C-terminally Amidated Peptides

The present invention concerns also a method for the production of C-terminus amidated peptides under high temperature conditions by use of prolylendopeptidase. Prolylendopeptidase catalyzes not only the hydrolytic cleavage of a peptide at the C-terminus side of a proline residue, but also, forming the peptide bond in the reverse manner of the hydrolysis, the coupling of a peptide fragment to C-terminus of the other fragment which is terminated by a proline residue. Under controlled conditions the coupling reaction is predominant and prolylendopeptidase is used to catalyze coupling of two peptide fragments (or of amino acid to a peptide fragment). The preferable conditions of the coupling are an excess of one of peptide fragments (or an amino acid), and the presence of an organic solvent, such as glycerol, ethylene glycol, butanediol, ethanol, n-propanol, i-propanol, acetonitrile, DMF, and DMSO, in a high concentration, typically more than 50%.

In preferable embodiments of the present invention, biologically active peptides whose C-termini are α-amidated and have proline residues, preferably, at or near their C-termini are prepared with prolylendopeptidase from two precursors thereof, wherein one of the precursors is a precursor peptide forming N-terminal region of the amidated bioactive peptide and having a proline residue at its C-terminus and another precursor is a precursor peptide or amino acid forming a C-terminal portion of the amidated bioactive peptide which precursor peptide or amino acid has been amidated at C-terminus. The α-amidated bioactive peptides prepared with prolylendopeptidase involve aspartocin, bermorphin, calcitonin, CGRP, CGRP II, crustacean erythrophore concentrating hormone, cockroach myoactive peptide I, color change hormone, glumitocin, granuliberin-R, isotocin, LH-RH, mesotocin, morphine modulating neuropeptide, α-MSH, oxytocin, phenypressin, $SCP_A$, $SCP_B$, valitocin, vasopressin, and vasotocin.

The present invention provides a process for the production of a recombinant DNA molecule comprising a gene coding for prolylendopeptidase, comprising the steps of preparing cDNA or genomic DNA from cells, preferentially bacterial cells, capable of producing prolylendopeptidase, inserting DNA fragments coding for prolylendopeptidase into a cloning vector, and selecting a hybrid vector containing the DNA coding for prolylendopeptidase.

The present invention concerns in particular the embodiments disclosed in the examples.

The present invention will now be further illustrated by, but is no means limited to, the following examples.

EXAMPLES

In the Examples, the following materials and methods are commonly used.

The bacterial strains and plasmids used are listed in Table 1.

TABLE 1

Strains and plasmids.

| Strains or plasmid | Relevant genotype |
| --- | --- |
| Strains | |
| E. coli | |
| JM 83 | ara,Δ(lac-proAB), rpsL(=strA), Ø80$^r$, lacZ ΔM15 |
| JM109 | recA1, endA1, gyrA96, thi, hsdR17, supE44, re1A1, λ$^-$, Δ(lac-proAB), F'[proAB$^+$, lacI$^q$, lacZ ΔM15, traD36] |
| HB 101 | F$^-$, hsdS20(r$^-_B$, m$^-_B$), recA13; ara-14, proA2, lacY1, galK2, rpsL20 (Sm$^r$), xyl-5, mtl-1, supE44, λ$^-$, mcrA$^+$, mcrB$^-$ |
| TG1 | supE, hsd Δ5, thi, D(lac-proAB), F'[proAB$^+$, lacI$^q$, lacZ ΔM15, traD36] |
| F. meningosepticum | IFO 12535 (ATCC 13253) |
| Plasmids | |
| pUC19 | Amp$^r$, lacI$^q$, lacZ' |
| pUC118 | Amp$^r$, lacI$^q$, lacZ', M13IG |
| pUC119 | Amp$^r$, lacI$^q$, lacZ', M13IG |
| pKK223-3 | Amp$^r$, P$_{tac}$, rrnB T$_1$T$_2$ |

Transformation, restriction mapping, preparation of plasmids, and other molecular cloning procedures are done by standard methods. (Sambrook, J. et al. "Molecular cloning: a laboratory manual," 2nd ed. 1989, Cold Spring Harbor Laboratory, Cold Spring Harbor; Silhavy, T. J. et al. "Experiments with gene fusions," 1984, Cold Spring Harbor Laboratory, Cold Spring Harbor). Restriction enzymes and DNA-modifying enzymes are used according to the recommendations of the manufacturers. Deletion with exonuclease III is carried out by use of a Kilo-Sequence Deletion kit (Yanisch-Perron, C. et al. Gene, 1985, 33, 103–119; Henikoff, S. Gene, 1984, 28, 351–359.). The nucleotide sequences are determined by the dideoxy method, by using a Sequenase kit. Genomic DNA from F. meningosepticum is isolated by the method of Saito and Miura (Saito, H. et al. Biochim. Biophys. Acta, 1963,72, 619–629). Oligonucleotides are synthesized with an Applied Biosystems Model 381A DNA synthesizer. After completion of the trityl-on synthesis the oligonuclotides are cleaved from the support and deprotected, following a standard protocol. The synthesized DNA is then purified by use of the Oligonucleotide Purification Cartridge according to the protocols of the manufacturer.

Restriction enzymes, DNA-modifying enzymes, the Kilo-Sequence Deletion kit and the MEGALABEL kit are purchased from Takara Shuzo Co. Ltd. (Kyoto). The Sequenase Ver.2.0 kit is the product of U.S. Biochemical Corp. (Cleveland, Ohio). Prolylendopeptidase from F. meningosepticum and Endoproteinase Asp-N are purchased from Seikagaku Corp. (Tokyo) and Boehringer Mannheim Co. Ltd. (Tokyo), respectively.

The Taq Dye Deoxy Terminator Cycle Sequencing kit and the Oligonucleotide Purification Cartridge are the products of Applied Biosystems, Inc. (Foster City, Calif.). The QIAGEN tip-100 is obtained from DIAGEN GmbH (Düsseldorf, FRG). The GENECLEAN II kit and the CIRCLE-GROW medium are the products of BIO 101, Inc. (Vista, Calif.). The nitrocellulose filter is purchased from Schleicher & Schuell (Keene, N.H.). The YM 30 ultrafiltration membrane is obtained from AMICON Inc. (Beverly, Mass.). The CM52 cation exchange resin is the product of Whatman Paper Ltd. (Maidstone, England). The enzyme substrates, Z-Gly-Pro-β-naphthylamide and Z-Gly-Pro-p-nitroanilide are obtained from Novabiochem AG (Laeufelfingen, Switzerland). Radio isotopes are purchased from Amersham Japan Co. Ltd. (Tokyo). Other biochemicals are purchased from Sigma Chemical Co. (St. Louis, Mo.), Wako Pure Chemical Industries Ltd. (Osaka, Japan) and Nacalai Tesque Inc. (Kyoto, Japan).

Example 1

Preparation of Starting DNA from *F. meningosepticum*

Commercially obtained prolylendopeptidase is purified by reverse phase HPLC on a 4.6×35 mm TSKgel Octadecyl NPR column (Tosoh Co. Ltd.). The column is eluted with 0.01% TFA in water and a 3:1 mixture of $CH_3CN$ and i-Propanol, at a flow rate of 1 ml/min. The gradient from 35–70% of the organic solvent mixture is applied over 40 min and the major peak is collected.

Since N-terminus of the endopeptidase is blocked, the enzyme must be subjected to proteolytic cleavage to determine its partial primary structure. The proteases commonly used for the cleavage like trypsin do not give satisfactory results. Therefore, proteases and conditions of the hydrolytic cleavage are systematically investigated and Endoproteinase Asp-N is found to give the best result.

The purified enzyme (0.5 mg) in 10 mM ammonium carbonate, pH 7.9, containing 4mM urea is hydrolyzed by 1 μg of Endoproteinase Asp-N at 37° C. for 24h. The peptide mixture obtained by this digestion is separated by reverse phase HPLC on a 4.6×250 mm Vydac C18 column (Separations Group Corp.) with the mobile phase of 0.01% TFA in water and a 3:1 mixture of $CH_3CN$ and i-PrOH. The flow rate is 1 ml/min. The isolated peptides are further purified by rechromatography. The amino acid sequence of the purified fragments are determined by manual Edman degradation using the methods described by Kobayashi and Tarr (Kobayashi, R. et al. Tanpakushitsu Kakusan Koso, 1986, 31, 991–1002; Tarr, G. E. "Methods in protein sequencing analysis" (ed. Elzinga, M.), 1982,223–232, Humana Press, New Jersey).

The nucleotide sequences for the probes are not uniquely determined from the amino acid sequences because of multiple codon usage. Out of the 23 partial amino acid sequences six which give relatively less combinations of possible nucleotide sequences are chosen to make DNA probes (Table 2). Preferred codon usage in *F. meningosepticum* has not been known, and two guidelines are adopted in the design of the nucleotide probes. Namely, three of the 6 probes (A-12, 13 and 19) are designed so as to consist of a single oligonucleotide sequence, selecting the most probable codon for each amino acid residue on the assumption that the genome DNA of *F. meningosepticum* is GC rich. The other three (A-3, 9 and 18) are mixtures of oligonucleotides of the possible sequences. To reduce further the number of the possible sequences in the mixture, inosine (I) is placed at the position which can be one of four bases, A, G, C and T, since inosine forms stable base pairs with all of four.

TABLE 2

Determined partial amino acid sequences of the fragments of prolylendopeptidase obtained by the Endoproteinase Asp-N digestion (shown by the amino acid residur No. in SEQ ID No. 8, and corresponding nucleotide positions in SEQ ID No. 1 of the probes designed from the amino acid sequences.

| Fragment No. | Amino acid residue No. in SEQ ID No. 8 | Probe No. | Corresponding nucleotide position in SEQ ID No. 1 |
|---|---|---|---|
| 3 | 499–509 | A-3 | 1811–1833 |
| 9 | 352–364 | A-9 | 1370–1407 |
| 12 | 28–34 | A-12 | 398–414 |
| 13 | 182–190 | A-13 | 860–877 |
| 18 | 380–391 | A-18 | 1454–1485 |
| 19 | 268–276 | A-19 | 1118–1137 |

Oligonucleotides are synthesized with an Applied Biosystems Model 381A DNA synthesizer. After removal of dimethoxytrityl group at the end of the synthetic sequence the oligonucleotides are deprotected and cleaved from the supports, according to the protocols of the manufacturer. The synthesized DNA are then subjected to preparative electrophoresis with 8% polyacrylamide gel in 7M urea. Purified oligonucleotides are extracted from the separated bands and deionized by use of Waters Sep-Pack C-18 columns.

The chromosomal DNA is isolated from *F. meningosepticum* and digested by 4 kinds of commonly used restriction enzymes recognizing hexanucleotide sequence, i.e., PstI, HindIII EcoRI and BglII.

Oligonucleotide probes are radio-labeled by use of a MEGALABEL kit with [$\gamma$-$^{32}$P]ATP to give a specific activity of ca. $1\times10^6$ cpm/pmol. The chromosomal fragments are electrophoresed on a 0.7% agarose gel and transferred to a Millipore nitrocellulose filter by the method described by Sambrook et al. (Sambrook et al., 1989, supra).

After prehybridization according to a standard protocol (Sambrook et al., 1989, supra), hybridization is carried out in 6× SSC hybridization solution with 0.2 pmol/ml of the labelled probe at 45° C. for 16 h. The filter is washed with 6× SSC three times for 3 min at room temperature and then once for 1 min at 45° C. Autoradiography is performed with a Fuji Bio-image analyzer BAS 2000. Only the A-3 probe is found to give a clear and specific signal with each of the digested DNA.

The molecular weight of prolylendopeptidase is found quite large, 76,000 by SDS-poly-acrylamide gel electrophoresis (Yoshimoto et al., 1980, supra). The size of the enzyme corresponds to 2 kb of the coding region in the genome. The larger the cloned DNA fragment is, the higher the chance of including the full length of the open reading frame. Therefore, rather a long fragment but small enough to get a high efficiency in the transformation is desired and 7 kb of the BglII fragment is selected. Namely, genomic DNA digested by BglII is subjected to preparative electrophoresis with low-melting-point agarose and the fraction of the gel containing 7 kb fragments is cut out. The excised gel piece is dissolved in a ligation mixture and the extracted chromosomal fragments are cloned into BamHI site of pUC19. By this ligation mixture *E. coli* HB101 is transformed to give a genomic library comprising about 4,000 clones.

The genomic library is screened with the A-3 probe by colony hybridization and 119 positive clones are obtained. Sixteen positive clones are chosen and analyzed further by restriction endonuclease digestion and the enzyme assay. One clone with 7 kb insert is found to show a comparatively high prolylendopeptidase activity. The plasmid is named pFPEP02 and further characterized. The restriction map of the insert of pFPEP02 is shown in FIG. 1. The entire nucleotide sequence of the 2.6 kb of HincII—EcoRI (shown in SEQ ID No. 1) fragment is determined by the dideoxy method from a series of deletion subclones generated from either end of a larger fragment which includes the 2.6 kb of HincII—EcoRI (pFPEP03, deposited as FERM BP-3466).

Plasmid pFPEPO2 is digested with HincII to obtain a 3.1 k bp HincII fragment containing prolylendopeptidase gene, which is then subcloned at the SmaI site of pUC118 by blunt end ligation to give pFPEPO4. After the ligation, the insertion points at the both ends of the fragment are cleavable neither by HincII nor SmaI. To delete the ScaI and PvuII sites in the coding region the synthetic double-stranded oligonucleotide fragment which corresponds to the sequence between the SmaI and PvuII sites but is mutated at two positions (with Synthetic Fragment I, see SEQ ID No. 2) is prepared by annealing the lower strand and the upper strand only whose 5' end has been phosphorylated beforehand by T4 polynucleotide kinase.

On the other hand, the plasmid pFPEPO4 is cleaved at the single SmaI site existing in the open reading frame, and the mutated SmaI—PvuII fragment mentioned above is ligated to the linearized plasmid at both terminus SmaI sites. The ligation product is then digested by SacI and the longer fragment, containing the 5' portion of the coding region, is isolated by agarose gel electrophoresis. After kinasing the isolated fragment the missing piece between PvuII and SacI sites, prepared separately from pFPEPO4, is ligated to construct plasmid pFPEPO4'. Since one nucleotide at the terminus generated by PvuII has been changed in the synthetic fragment, the PvuII site is not regenerated by this cyclization.

Next, a new EcoRI site is created immediately upstream from the initiation codon of the prolylendopeptidase gene as follow. Synthetic Fragment II (SEQ ID No.3) is prepared by ligation of the four oligonucleotides U1, U2, L1 and L2 (see SEQ ID No.4, 5, 6 and 7, respectively), where two of them (U2 and L1) have been phosphorylated at their 5' termini. The prepared fragment corresponds from the initiation codon to PvuII site in the upstream coding region and has protruding cohesive 5' terminus immediately upstream of the initiation site to introduce EcoRI site after ligation. For the following ligation the both 5' ends of the prepared fragment are phosphorylated by T4 polynucleotide kinase.

The plasmid pFPEPO4', in which one of four PvuII has been deleted, is digested with PvuII, and the fragment containing most of the coding region is isolated by agarose gel electrophoresis and ligated to the second synthetic fragment described above. The product obtained by the ligation is digested with EcoRI to isolate the complete open reading frame with the 5' protruding cohesive ends at both termini, which is then subcloned at the EcoRI site of pUC119. The two synthetic regions in the obtained plasmid, pFPEP-EE, are sequenced and the mutated nucleotide sequences are confirmed. The resulting plasmid is pFPEP-EE.

In the next step of the vector construction, the whole coding region, together with a short downstream non-coding region, is cleaved out from pFPEP-EE by EcoRI. The fragment is then inserted into the EcoRI site of the expression vector, pKK223-3, to provide pKK-FPEP in which the transcription of the prolylendopeptidase gene is under the control of the tac promoter.

The replication origin of pKK223-3 originates from pBR322 and the copy number of this expression vector in a single cell is usually low. Because of the higher dose effect of the gene a high copy number plasmid is preferable as an expression vector for a higher expression level. Therefore, a) a set of the promoter and the coding region or b) a set of the promoter, the coding region and the terminator is excised by BamHI or BbiII, respectively, and transplanted into the high copy number plasmid, pUC119. Since the peptidase gene is transferred from pKK-FPEP together with the tac promoter, the original lac promoter of pUC119 is removed by PvuII in order to avoid the double promoter. In between the blunt ends generated by this PvuII digestion either the gene set a) or the set b), which has been blunted by T4 DNA polymerase, is inserted to give pUK-FPEP-a or pUK-FPEP-b, respectively (FIG. 2).

Example 2

Random Mutagenesis of the Starting DNA by Chemical Treatment

Figure 2:
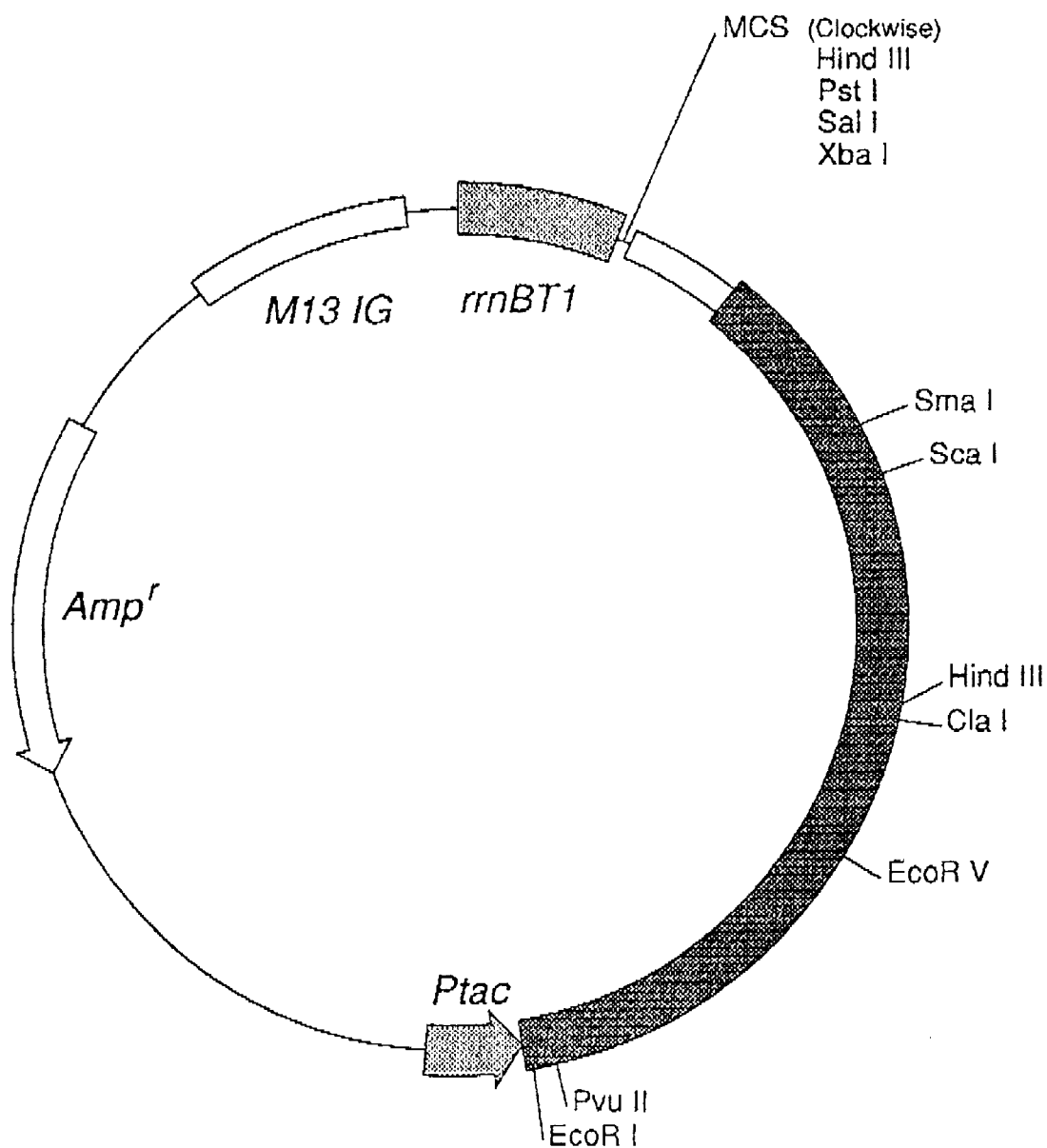
FIG. 2 represents schematically expression plasmid pUK-FPEP-b. The tac promoter is followed by the structure gene of prolylendopeptidase (shaded darkly), the multiple cloning site (MCS) and the *E. coli* rrnB T1 transcription terminator. The plasmid carries the M13 IG region which enables preparation of the single stranded DNA with the aid of a helper bacteriophage.

The plasmid pUK-FPEP-b is digested with EcoRI and PstI (FIG. 2). The 2.3 kb DNA fragment containing the prolylendopeptidase gene is separated from the major fragment of the plasmid (the vector fragment) and subcloned into pUC118 or PUC119. The single-stranded DNA of the recombinant plasmids is prepared by the aid of an M13 helper phage and treated at 20° C. with 1 M sodium nitrite in 0.25 M sodium acetate, pH 4.3, for 15–20 min, 3 M formic acid for 5–20 min or 20% hydrazine for 5–20 min by the method of Myers et al. (Science, 1985, 229, 242–247). The chemically mutagenized single-stranded DNA is made into a duplex form by avian myeloblastosis virus (AMV) reverse transcriptase. The resulting 2.3 kb fragment is ligated back with the vector fragment to re-construct the expression plasmid, pUK-FPEP-b.

Example 3

Screening for Heat-stable Prolylendopeptidase

With the ligation mixture obtained in the Example 2, *E. coli* is transformed and plated out on nitrocellulose filters placed on the TY agar plates (1% Bacto-tryptone, 0.1% glucose, 0.8% NaCl, 1.5% agar, pH 7.0) containing 60 μg/ml ampicilin. These plates are incubated at 37° C. and, when colonies appear on the filters, a replica of colonies on each filter is made on another filter. Both original and replica filters are incubated on the agar plates at 37° C. for a few hours. The originals are then stored at 4° C. and the replicas subjected to cell lysis.

The cell lysis is performed by soaking the filters at room temperature sequentially in two lysis buffers; first 2 mg/ml lysozyme in 50 mM Tris-HCl (pH 8.0) for 20 min and secondly 1% Triton X-100 in 50 mM Tris-HCl (pH 8.0) for 5 min. The bacterial debris is gently scraped from the surface of the filters in 20 mM sodium phosphate (pH 7.0). The filters are then blocked with.3% BSA in 20 mM sodium phosphate (pH 7.0) or 5% skim milk in the same buffer to prevent non-specific adsorption on the filters of a substrate peptide for following active staining of prolylendopeptidase. After washing out the blocking buffer with 20 mM sodium phosphate (pH 7.0), the filters are incubated in 20 mM sodium phosphate (pH 7.0) at 50° C. for 15 min. To identify clones that carry residual activity of the enzyme after the heat-treatment, the filters are subjected to the active staining with 0.1 mM Z-Gly-Ala-Pro-β-naphthylamide and 0.01%

Fast Garnet GBC sulfate salt. The colonies producing heat-stable prolylendopeptidase are visualized as red spots on the filters by the formation of an insoluble coupling product of the Fast Garnet and the hydrolysis product of the substrate, β-naphthylamine. The clones corresponding to the stained colonies are isolated from the original filters separately stored at 4° C.

By this method 24,000 colonies are screened and 134 clones are picked up as candidates producing heat-stable prolylendopeptidase. The isolated clones are then gridded onto a few nitrocellulose filters placed on the agar plates, and replicas of each filter are prepared again and subjected to the secondary screening. In the secondary screening the replicas are each treated with a gradually increased temperature until identification of the clone producing the most heat-stable prolylendopeptidase (PEP-15).

Example 4

Purification of the Heat-stable Prolylendopeptidase

Throughout the purification steps, prolylendopeptidase activity is assayed as follows. To 0.94 ml of 0. 1 M potassium phosphate (pH 7.0), 100 μg/ml bovine serum albumin, 1 mM DTT, is added 0.05 ml of 4 mM Z-Gly-Pro-p-nitroanilide (Z=N-benzyloxycarbonyl) in 40% dioxane. After 3 min preincubation at 30° C., 0.01 ml of a diluted solution of the enzyme is added to the mixture and changes of the adsorbance at 410 nm are followed with a Hitachi spectrophotometer U-3210 at 30° C. One unit of the enzyme activity is defined as the amount of the enzyme that releases 1 μmol of p-nitroaniline per minute, corresponding to 8.87 OD/min with this standard procedure.

The *E. coli* clone obtained by the screening for a heat-stable prolylendopeptidase (Example 3) is grown in 500 ml of a CIRCLEGROW medium containing 60 μg/ml ampicillin at 37° C. After 12 hr, IPTG (1 mM) is added and the culture is continued for additional 16 hr. The *E. coli* cells are harvested by centrifugation and washed with cold 0.1 M Tris-HCl (pH 8.0). The following purification procedures are carried out at 4° C. unless otherwise specified. The washed cells are re-suspended in 50 ml of 0.1 M Tris-HCl (pH 8.0), 0.5 M sucrose, 5mM EDTA. Lysozyme is added to a final concentration of 160 μg/ml, and then the same volume of ice-cold water is added. After incubation for 30 min on ice, spheroplasts formed by the osmotic shock and lysozyme treatment are removed by centrifugation at 10,000×g for 20 min. The supernatant (the periplasmic fraction) is diluted again with the same volume of ice-cold water and the pH is adjusted to 7 with 1 N HCl. The diluted solution is applied to a CM 52 column that has been equilibrated with 20 mM sodium phosphate (pH 6.2). The enzyme is eluted by a linear gradient from 0 to 0.25 M NaCl. The active fractions are pooled and concentrated using an Amicon ultrafiltration cell with a YM 30 membrane, and the concentrate is dialyzed against 20 mM sodium phosphate (pH 6.2). The purified heat-stable prolylendopeptidase, PEP-15 is judged to be homogenous by SDS polyacrylamide gel electrophoresis.

Example 5

Heat Stability of the Mutated Prolylendopeptidase

The specific activity of PEP-15 is found to be 87 units/mg protein, close to the wild type enzyme (124 units/mg protein). The heat-stability of the heat-stable prolylendopeptidase is compared with the wild-type with regard to relative rates of losing activity by heat treatment. Each solution of the heat-stable prolylendopeptidase and the wild-type prolylendopeptidase in 20 mM sodium phosphate, pH 7.0 (1 mg/ml) is incubated at 54° C. and aliquots are removed and assayed for residual enzyme activity after various time intervals over 120 min. When the relative activities of the heat-stable prolylendopeptidase and the wild-type prolylendopeptidase are plotted as a function of incubation time, both give linear relation in semilogarishmic plots, indicating the loss of the activities obeyed first-order kinetics. From the slopes of the lines, the rate constants of the heat inactivation for the wild-type and the heat-stable prolylendopeptidase are estimated to be $2.17 \times 10^{-2}$ and $6.24 \times 10^{-3}$ $min^{-1}$, respectively. The rate constants clearly demonstrate that PEP-15 is stabilized by a factor of 3.5 at 54° C.

Example 6

DNA Sequencing of the Mutated Gene Encoding for PEP-15

To confirm a change in the amino acid sequence of PEP-15, nucleotide sequence of the mutated gene is determined. The expression plasmid is isolated from the clone producing PEP-15 using a QIAGEN tip-100, according to the procedure recommended by the supplier. To determine whole sequence of the mutated prolylendopeptidase gene, 22 sequencing primers that cover all the coding region are synthesized, and the nucleotide sequence is determined by an Applied Biosystems Model 307A DNA sequencer using the Tag Dye Deoxy Terminator Cycle Sequencing kit. The nucleotide sequence coding for PEP-15 is compared with that of the wild-type to reveal the substitution of nucleotide G to A leading to the insertion of Lys instead of Glu at the amino acid position 477.

The coding region was recloned in the native vector fragment in order to prepare expression vector pUK-FPEP-15.

Example 7

Random Mutagenesis Using a Modified PCR Method

In another embodiment of the present invention polymerase chain reaction (PCR) method is adopted to generate random mutagenesis in the structure gene of prolylendopeptidase. The PCR mutagenesis, on the contrary to the chemical mutagenesis, amplifies a region of the gene to be mutated under conditions that reduce the fidelity of DNA synthesis by Taq polymerase. The 2.3 kb EcoRI-PstI DNA fragment of pUK-FPEP-b encoding the prolylendopeptidase is amplified with a pair of 25 nucleotides primers, which are complementary to the regions immediately flanking the EcoRI and PstI sites.

To introduce a limited number of, i.e., a single or at most a few, base substitutions efficiently in the prolylendopeptidase gene, effects of several factors on the fidelity of the polymerase are examined. The factors investigated involve addition of $MnCl_2$ or DMSO, alteration on $MgCl_2$ concentration, and the deoxy nucleotide pool imbalance. A basic reaction mixture contains, 10 mM Tris HCl (pH 8.3), 50 mM KCl, 1.5 mM $MgCl_2$, 0.01% (w/v) bovine serum albumin, 0.2 mM each of four dNTP's, 10 ng/ml of the template plasmid, 1 μM each primers and 25 units/ml Taq polymerase, and the modifications of the basic reaction mixture used in the present invention are as follows (modifications are made in five different experiments):

1) 50–100 μM of $MnCl_2$ is added with an increased concentration (5 mM) of $MgCl_2$.

2) 5–20% of DMSO is added.
3) The concentration of MgCl$_2$ is changed from 5 mM to 10 mM.
4) The concentrations of dGTP, dTTP and dCTE are held constant at 1 mM while the concentration of dATP is lowered from 0.2 mM to 0.1 mM in the presence of 5 mM MgCl$_2$.
5) While the concentrations of dATP, dCTP and dTTP are held constant at 0.1 mM, the concentration of dGTP is varied from 0.5 mM to 1 mM in the presence of 1.5–2 mM MgCl$_2$.

All five modifications of the basic reaction mixture give many clones producing heat stable prolylendopeptidase. For improving heat stability, the modifications are repeated or different of the above modification methods are applied sequentially.

In the present invention, FPEP-227 was prepared from wild type by modification 3), FPEP-361 from FPEP-227 by modification 1), and FPEP-407 from FPEP-361 by modification 3).

The PCR is carried out by using Gene Amp™ PCR system 9600 (Perkin-Elmer) by melting the template DNA at 94° C. for 1 min and annealing with the primers at 50° C. for 1 min. Chain extension is initiated at 70° C. for 4 min and a total of 25 cycles are performed. After the last cycle, the polymerization at 70° C. is extended for additional 7 min. To construct a randomly mutated DNA library, the amplified DNA fragment is digested with EcoRI and PstI and purified by the GENECLEAN II kit. The resultant 2.3 kb EcoRI-PstI fragment is ligated back to the intact vector fragment of pUK-FPEP-b.

The first cycle of the PCR mutagenesis is started from the wild-type gene. About 80,000 clones are generated by the PCR and screened by the same method as described in Example 3 but with a slightly higher temperature (52° C.) of the heat treatment, which yields a clone producing the most heat-stable prolylendopeptidase in the mutant library, PEP-227.

Example 8

Repeating Random Mutagenesis Using a Modified PCR Method

Since accumulation of stabilizing mutations in a single molecule of the enzyme is expected to result in an even larger improvement in the stability than that obtained with FPEP-15 or FPEP-227, the PCR mutagenesis/screening cycle is repeated sequentially to accumulate mutations.

The isolated clone coding for FPEP-227 (pUK-FPEP-227) is used as a template for the second cycle of the PCR mutagenesis to give a library consisting of about 40,000) clones. Screening of the second generation library is performed similarly to yield that clone expressing the most heat-stable prolylendopeptidase (PEP-361). In the third cycle the mutagenesis and screening are repeated once again starting from the expression plasmid encoding for PEP-361 (pUK-FPEP-361) as a template. The temperature of the heat-treatment is gradually increased as the cycle of the mutagenesis/screening proceeds and, in the third cycle, that clone producing the most heat-stable prolylendopeptidase (PEP-407) is identified among 50,000 clones by the screening with the heat-treatment at 61° C.

It should be noted that the clones isolated and characterized in the present examples are not the only clones that are prepared and are identified as coding for heat-stable enzymes. The clones specified herein are only isolated as examples in order to teach the principle of the method.

Example 9

Isolation and Characterization of Highly Heat-stable Prolylendopeptidase

From the clones producing the heat-stable prolylendopeptidases PEP-227, PEP-361 and PEP-407, expression plasmids are isolated and named pUK-FPEP-227, pUK-FPEP-361 and pUK-FPEP-407, respectively. The DNA sequences of the mutated structure genes carried on the plasmids are determined to follow structure changes in the amino acid sequence of prolylendopeptidase. It is found that a single or a few base substitutions are introduced in each random mutagenesis/screening cycle and it is also confirmed that the mutations are accumulated in the gene by the sequential mutagenesis/screening cycles (Table 3).

TABLE 3

Base substitutions identified in mutated genes encoding heat-stable prolylendopeptidase and resulting amino acid replacements

| pUK-FPEP-227 | pUK-FPEP-361 | pUK-FPEP-407 |
| --- | --- | --- |
| 458 G → C (E48Q) | 458 G → C (E48Q) | 458 G → C (E48Q) |
|  | 701 G → A (A129T) | 701 G → A (A129T) |
|  | 2,214 G → T (G633V) | 2,214 G → T (G633V) |
|  | 2,239 T → C (silent) | 2,239 T → C (silent) |
|  |  | 467 T → C (F51L) |

Figure 3:
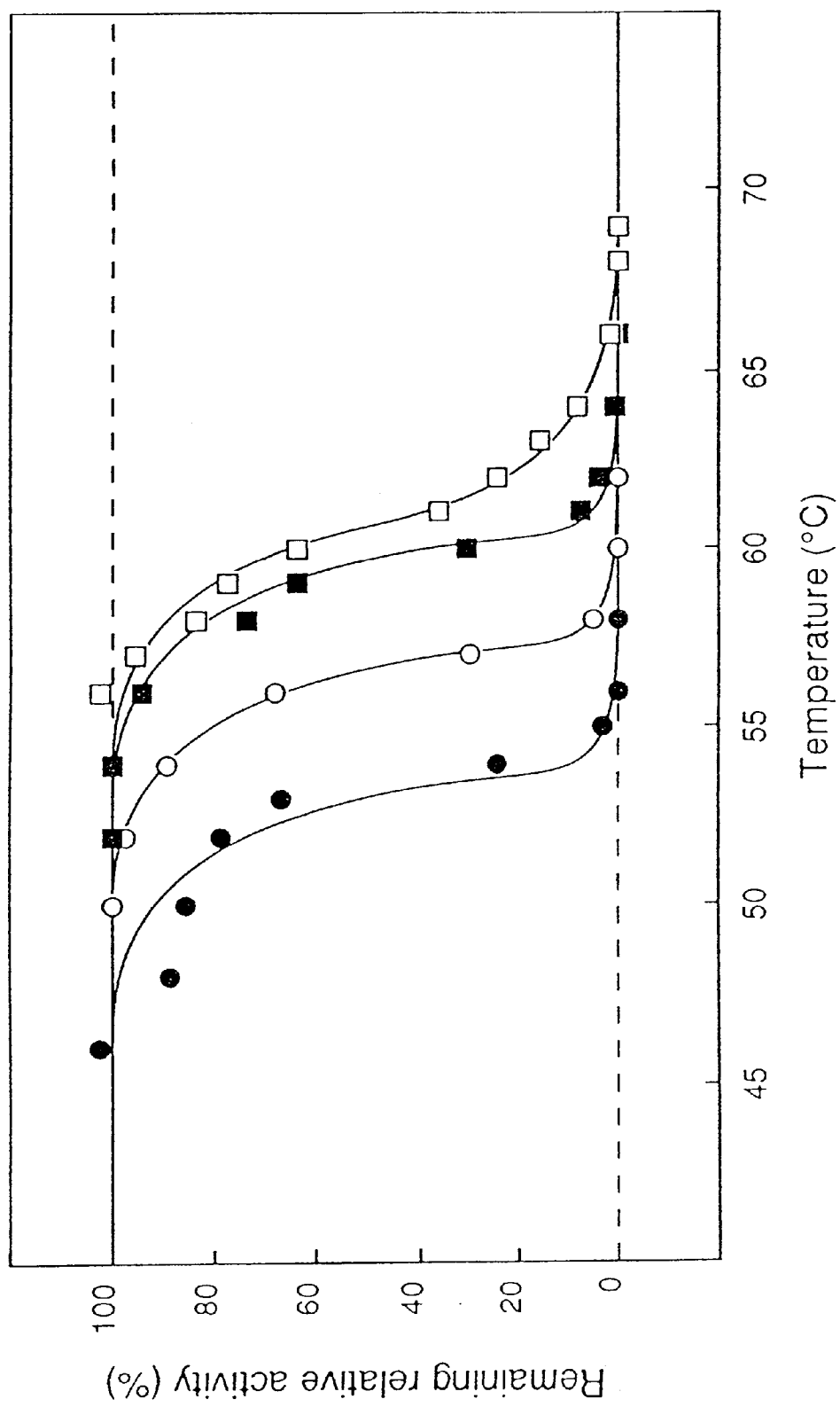
FIG. 3 represents thermal inactivation curves of the wild type and heat-stable prolylendopeptidases. Each solution of the wild type (filled-in circles) and the heat-stable prolylendopeptidases, PEP-227 (circles), PEP-361 (filled-in squares) and PEP-407 (open squares), in 20 mM sodium phosphate (pH 7.0) is incubated at variant temperatures for 30 min and remaining activity of prolylendopeptidase is measured. The residual activities are shown as functions of temperature.

The specific activities of the purified heat-stable prolylendopeptidases, PEP-227, PEP-361 and PEP-407 are found to be 116, 87 and 69 units/mg protein, respectively. The specific activities of the heat-stable prolylendopeptidases are comparable with that of the wild-type (124 units/mg protein) but shows a tendency to decrease as the amino acid replacements are accumulated. First, the heat-stability of the heat-stable prolylendopeptidases are evaluated with values of $T_{50}$, at which temperature the enzyme loses 50% activity in 30 min. In 20 mM sodium phosphate (pH 7.0), 0.2 mg/ml of the wild-type or one of the heat-stable prolylendopeptidases is incubated in Gene Amp™ PCR system 9600 (Perkin-Elmer) for 30 min at various temperatures ranging from 46 to 69° C. The residual activities are measured and plotted as a function of the temperature (FIG. 3). While the $T_{50}$ of the wild-type is estimated to be 53.5° C. from the figure, the $T_{50}$ of the heat-stable prolylendopeptidases, PEP-227, PEP-361 and PEP-407 shifts upward to 56.5, 59.5 and 60.5° C., respectively. The changes of the $T_{50}$, as an indication of heat-stability, clearly demonstrate the heat-stability of prolylendopeptidase is improved as the mutagenesis/screening cycle proceeds.

To evaluate more quantitatively the improvements of the heat-stability, the enzyme solutions are incubated at a constant temperature and changes in the remaining activities are followed over 120 min. In 20 mM sodium phosphate (pH 7.0), 0.2 mg/ml of each enzyme solution is incubated at 60° C. At various time intervals, aliquots are removed and residual activities are measured. All heat-inactivation processes of the wild-type and the three heat-stable prolylendopeptidases obeyed the first order kinetics, showing lines when residual activities are plotted semilogarithmically as functions of incubation time. The inactivation rate contants of the wild-type, PEP-227, PEP-361. and PEP-407 are estimated from the slopes to be $4.27 \times 10^{-1}$, $7.08 \times 10^{-2}$ $1.32 \times$ $10^{-2}$ and $7.16 \times 10^{-3}$ min$^{-1}$, respectively. The rate constants demonstrate large improvements in stabilities of the heat-stable prolylendopeptidases: the improvement reaches factors of 60 with the most heat-stable prolylendopeptidase obtained in the final cycle of the mutagenesis/screening.

Deposited Microorganisms

E. coli TG1/pFPEPO3 was deposited under the Budapest Treaty with the DSM—Deutsche Sammlung von Mikroorganismen und Zellkulturen GmbH, Mascheroder Weg 1b, D-38124 Braunschweig, Federal Republic of Germany, as DSM 9250 on Jun. 16, 1994.

What is claimed is:

1. A heat-stable prolylendopeptidase selected from the group consisting of heat-stable prolylendopeptidases having the amino acid sequence as set forth in SEQ ID No. 8 with amino acid Glu in position 48 ("Glu48"), Phe51, Ala129, Glu477 or Gly633 replaced by an amino acid other than proline.

2. The heat-stable prolylendopeptidase according to claim 1, selected from the group consisting of heat-stable prolylendopeptidases having the amino acid sequence as set forth in SEQ ID No.8 with amino acid Glu48 replaced by Gln, amino acid Phe51 replaced by Leu, amino acid Ala129 replaced by Thr, amino acid Glu477 replaced by Lys or amino acid Gly633 replaced by Val.

3. The heat-stable prolylendopeptidase according to claim 1, selected from the group consisting of heat-stable prolylendopeptidases having the amino acid sequence as set forth in SEQ ID No. 8 with amino acid(s) (a) Glu48, (b) Glu48, Ala129 and Gly633, (c) Glu48, Phe51, Ala129 and Gly633, or (d) Glu477 replaced by an amino acid other than proline.

4. The heat-stable prolylendopeptidase according to claim 1, selected from the group consisting of heat-stable prolylendopeptidases having the amino acid sequence as set forth in SEQ ID No.8 with amino acid(s) (a) Glu48 replaced by Gln (PEP-227), (b) Glu48 replaced by Gln, Ala129 replaced by Thr and Gly633 replaced by Val (PEP-361), (c) Glu48 replaced by Gln, Phe51 replaced by Leu, Ala129 replaced by Thr, Gly633 replaced by Val (PEP-407), or (d) Glu477 replaced by Lys (PEP-15).

5. A recombinant DNA comprising a DNA sequence coding for a heat-stable prolylendopeptidase selected from the group consisting of heat-stable prolylendopeptidases having the amino acid sequence as set forth in SEQ ID No. 8 with amino acid Glu48, Phe51, Ala129, Glu477 or Gly633 replaced by an amino acid other than proline.

6. A recombinant DNA selected from the group consisting of recombinant DNAS coding for the amino acid sequence as set forth in SEQ ID No. 8 with codon for amino acid Glu48, Phe51, Ala129, Glu477 or Gly633 replaced by a codon coding for an amino acid other than proline.

7. The recombinant DNA according to claim 5, comprising a DNA sequence coding for a heat-stable prolylendopeptidase selected from the group consisting of heat-stable prolylendopeptidases having the amino acid sequence as set forth in SEQ ID No. 8 with amino acid Glu48 replaced by Gln, amino acid Phe51 replaced by Leu, amino acid Ala129 replaced by Thr, amino acid Glu477 replaced by Lys or amino acid Gly633 replaced by Val.

8. The recombinant DNA according to claim 6, selected from the group consisting of recombinant DNAs coding for the amino acid sequence as set forth in SEQ ID No. 8 with the codon coding for amino acid Glu48 replaced by a codon coding for amino acid Gln, the codon coding for amino acid Phe51 replaced by a codon coding for amino acid Leu, the codon coding for amino acid Ala129 replaced by a codon coding for amino acid Thr, the codon coding for amino acid Glu477 replaced by a codon coding for Lys or the codon coding for amino acid Gly633 replaced by a codon coding for amino acid Val.

9. The recombinant DNA according to claim 5, comprising a DNA sequence coding for a heat-stable prolylendopeptidase selected from the group consisting of heat-stable prolylendopeptidases having the amino acid sequence as set forth in SEQ ID No. 8 with amino acid(s) (a) Glu48, (b) Glu48, Ala129 and Gly633, (c) Glu48, Phe51, Ala129 and Gly633, or (d) Glu477 replaced by an amino acid other than proline.

10. The recombinant DNA according to claim 6, selected from the group consisting of recombinant DNAs coding for the amino acid sequence as set forth in SEQ ID No. 8 with the codon(s) coding for amino acid(s) (a) Glu48, (b) Glu48, Ala129 and Gly633, (c) Glu48, Phe51, Ala129 and Gly633, or (d) Glu477 replaced by codons coding for an amino acid other than proline.

11. The recombinant DNA according to claim 5, comprising a DNA sequence coding for a heat-stable prolylendopeptidase selected from the group consisting of heat-stable prolylendopeptidases having the amino acid sequence as set forth in SEQ ID No. 8 with amino acid(s) (a) Glu48 replaced by Gln (PEP-227), (b) Glu48 replaced by Gln, Ala129 replaced by Thr and Gly633 replaced by Val (PEP-361), (c) Glu48 replaced by Gln, Phe51 replaced by Leu, Ala129 replaced by Thr, Gly633 replaced by Val (PEP-407), or (d) Glu477 replaced by Lys (PEP-15).

12. The recombinant DNA according to claim 6, selected from the group consisting of recombinant DNAs coding for the amino acid sequence as set forth in SEQ ID No. 8 with (a) the codon coding for amino acid Glu48 replaced by a codon coding for amino acid Gln, (b) the codon coding for amino acid Glu48 replaced by a codon coding for amino acid Gln, the codon coding for amino acid Ala129 replaced by a codon coding for amino acid Thr and the codon coding for amino acid Gly633 replaced by a codon coding for amino acid Val, (c) the codon coding for amino acid Glu48 replaced by a codon coding for amino acid Gln, the codon coding for amino acid Phe51 replaced by a codon coding for amino acid Leu, the codon coding for amino acid Ala129 replaced by a codon coding for amino acid Thr, the codon coding for amino acid Gly633 replaced by a codon coding for amino acid Val, or (d) the codon coding for amino acid Glu477 replaced by a codon coding for amino acid Lys.

13. The recombinant DNA according to claim 6, selected from the group consisting of recombinant DNAs having the nucleotide sequence as set forth in nucleotides 317 to 2374 of SEQ ID No. 1 with (a) the nucleotide G at position 458 ("458 G") replaced by C, (b) nucleotide 458 G replaced by C, nucleotide 701 G replaced by A and nucleotide 2214 G replaced by T, (c) nucleotide 458 G replaced by C, nucleotide 467 T replaced by C, nucleotide 701 G replaced by A and nucleotide 2214 G replaced by T, or (d) nucleotide 1745 G replaced by A.

14. The hybrid vector, selected from the group consisting of pUK-FPEP-5, pUK-FPEP-227, pUK-FPEP-361 and pUK-FPEP-407.

15. The recombinant DNA according to claim 6, selected from the group consisting of recombinant DNAs having the nucleotide sequence as set forth in SEQ ID No. 1 with (a) the nucleotide G at position 458 ("458 G") replaced by C, (b) nucleotide 458 G replaced by C, nucleotide 701 G replaced by A and nucleotide 2214 G replaced by T, (c) nucleotide 458 G replaced by C, nucleotide 467 T replaced by C, nucleotide 701 G replaced by A and nucleotide 2214 G replaced by T, or (d) nucleotide 1745 G replaced by A.

* * * * *

UNITED STATES PATENT AND TRADEMARK OFFICE
CERTIFICATE OF CORRECTION

PATENT NO. : 6,156,554
DATED : December 5, 2000
INVENTOR(S) : Inaoka et al.

Page 1 of 1

It is certified that error appears in the above-identified patent and that said Letters Patent is hereby corrected as shown below:

Column 40, claim 6,
Line 2, should read -- of recombinant DNAs coding for the amino acid sequence --.

Column 42, claim 14,
First word should read -- A --.
Line 2, beginning of said claim should read -- of pUK-FPEP-15, --.

Signed and Sealed this

First Day of January, 2002

Attest:

JAMES E. ROGAN
Attesting Officer
Director of the United States Patent and Trademark Office

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 2636 base pairs
      (B) TYPE: nucleic acid
      (C) STRANDEDNESS: double
      (D) TOPOLOGY: linear (ii) MOLECULE TYPE: DNA (genomic)

(iv) ORIGINAL SOURCE:
      (A) ORGANISM: Flavobacterium meningosepticum (ix) FEATURE:
      (A) NAME/KEY: promoter
      (B) LOCATION: 1..259

(ix) FEATURE:
      (A) NAME/KEY: CDS
      (B) LOCATION: 260..316
      (D) OTHER INFORMATION: /function= "signal sequence"

(ix) FEATURE:
      (A) NAME/KEY: CDS
      (B) LOCATION: 317..2374
      (D) OTHER INFORMATION: /product= "coding region for mature prolylendopeptidase"

(ix) FEATURE:
      (A) NAME/KEY: misc_feature
      (B) LOCATION: 2375..2377
      (D) OTHER INFORMATION: function= "Stop codon"

(xi) SEQUENCE DESCRIPTION: SEQ ID NO:1:

```
GTTGACGGTA AAGTAGTATT TACTAAAAAG AGAGATAACA GGTCTTACGT ATCTGTAGCA       60

CCAGATGCTT AATTAAAGCA TTTTATAAAA ATTAAAACCT CAACGAAAGT TGAGGTTTTT      120

TTTGTCTCAA AAACCTAACA GGTTTCTGAA ACCTGTTAGG TTTATTGTGT ATAGGGGTTA      180

AGTGATACAT ATTTATACTG TGCTGAAATG CGAATCTGAT TATTCGAAAA TTCTCCCTAT      240

TTTTGATAAA ACCAATTCTA TGAAGTACAA CAAACTTTCT GTGGCAGTTG CAGCCTTTGC      300

TTTTGCAGCT GTATCAGCAC AAAATTCTAA TGTTTTGAAA TATCCCGAAA CTAAAAAAGT      360

AAGCCATACC GATACCTATT TTGGTACTCA GGTATCCGAT CCTTATCGCT GGCTGGAAGA      420

CGACAGAGCC GAAGATACAA AAGCCTGGGT ACAACAGGAA GTTAAATTTA CACAAGACTA      480

CCTTGCACAG ATTCCTTTCC GTGATCAGCT TAAAAAGCAA TTAATGGACA TCTGGAATTA      540

TGAGAAAATT TCAGCACCGT TTAAAAAAGG TAAATACACC TATTTTTCTA AAAATGATGG      600

TCTTCAGGCG CAATCTGTAC TTTACAGAAA AGATGCGGCA GGTAAGACGG AAGTATTTTT      660

AGATCCTAAT AAGTTTTCGG AAAAAGGAAC CACTTCTCTG GCAAGTGTTT CTTTTAATAA      720

AAAAGGAACT CTGGTCGCTT ATAGTATATC AGAAGGAGGT TCGGACTGGA ATAAGATTAT      780

TATTCTGGAT GCGGAAACCA AAAAGCAACT TGATGAAACT CTATTGGATG TTAAGTTCAG      840
```

```
TGGAATTTCA TGGTTGGGAG ATGAAGGATT CTTTTATTCC AGCTATGATA AGCCAAAAGA    900

AGGAAGCGTA CTTTCCGGGA TGACAGATAA ACACAAAGTT TATTTTCATA AGTTAGGAAC    960

GAAGCAGTCT CAGGATGAAT TGATTATTGG GGGTGATAAA TTTCCAAGAA GATATATAGG   1020

AGCTTATGTA ACCGATGATC AGAGATATCT GGTGGTTTCG GCTGCAAATG CAACCAACGG   1080

AAACGAGCTT TACATTAAAG ACCTGAAGAA TAAAACAGAT TTTATTCCGA TTATTACAGG   1140

TTTTGATAGC AATGTAAATG TTGCAGATAC CGACGGTGAT ACGCTTTATT TGTTCACCGA   1200

TAAAGATGCA CCGAATAAGC GACTGGTAAA ACAACGATT CAGAATCCAA AAGCGGAAAC    1260

ATGGAAAGAT GTGATTGCTG AAACCACCGA ACCATTCCAA ATCAATACGG GAGGCGGTTA   1320

TTTCTTTGCT ACTTATATGA AAGATGCAAT CGATCAGGTA AAGCAATATG ATAAAAACGG   1380

AAAGCTTGTA AGGGCTATAA AATTACCGGG AAGTGGTAAT GCAAGCGGTT TTGGGGGTGA   1440

AAAAACGGAA AAGGATCTGT ATTACTCTTT CACCAATTAT ATTACGCCGC CAACGATCTT   1500

TAAATATAAT GTAACAACAG GTAATTCTGA AGTTTACCAG AAGCCGAAAG TGAAGTTCAA   1560

TCCGGAAAAT TATGTTTCGG AGCAGGTATT CTATACTTCA TCTGACGGGA CTAAGATTCC   1620

GATGATGATC AGCTACAAGA AAGGCCTGAA AAAGACGGT AAAAACCCTA CAATATTATA    1680

CAGCTACGGA GGATTTAATA TCAGTCTTCA GCCTGCTTTC TCTGTTGTAA ATGCAATCTG   1740

GATGGAAAAC GGTGGTATTT ATGCTGTTCC GAATATCCGT GGTGGTGGAG AATATGGTAA   1800

GAAATGGCAT GATGCCGGAA CTAAAATGCA GAAAAGAAT GTATTTAATG ACTTTATTGC    1860

AGCCGGAGAG TACTTACAGA AAAACGGTTA TACATCTAAG GAATATATGG CGCTTTCCGG   1920

ACGTTCCAAC GGCGGTCTTC TTGTAGGGGC TACGATGACA ATGCGCCCTG ATTTGGCAAA   1980

AGTTGCATTC CCGGGAGTAG GAGTACTGGA TATGCTTCGT TATAATAAGT TTACAGCTGG   2040

TGCCGGTTGG GCTTATGATT ACGGTACAGC AGAAGACAGC AAGGAAATGT TTGAATACCT   2100

GAAGTCTTAT TCTCCGGTAC ATAACGTAAA AGCCGGAACT TGTTATCCTT CTACGATGGT   2160

CATTACAAGT GATCATGATG ACAGAGTTGT TCCCGCTCAT TCATTTAAGT TCGGTTCAGA   2220

ATTACAGGCA AACAATCTT GTAAGAATCC TATTCTTATC CGTATTGAAA CAAATGCTGG    2280

ACACGGAGCA GGACGTTCCA CAGAACAGGT CGTTGCTGAG AATGCCGATC TGCTTTCATT   2340

CGCATTATAT GAAATGGGAA TTAAAAGTTT AAAATAGATT TCAAATACTA AATATAAAAC   2400

AGGCAGGTCT TTTTGATTTG CCTGTTTTTT TATGATACTA TTGAGTTTGG ATTATGTTAA   2460

ATAGATTAGA TCATGAGATT TATATCTCAG GAAATGATTA ACTTTAATAC AAAATCTTAT   2520

ACAATGGAAA ATCATGACAT GACAACTTTA GTACAGGTAA TGAATACTTT GAAAAGAAGA   2580

GGCGTGGACA AAGAAATCCA GATGACAGAT GATAGGAAAT TTATACTTCA GAATTC       2636
```

(2) INFORMATION FOR SEQ ID NO:2:

(i) SEQUENCE CHARACTERISTICS:
        (A) LENGTH:  44 base pairs
        (B) TYPE:  nucleic acid
        (C) STRANDEDNESS:  double
        (D) TOPOLOGY:  linear (ii) MOLECULE TYPE:  DNA (genomic)

(ix) FEATURE:
        (A) NAME/KEY:  misc_feature
        (B) LOCATION:  1..44
        (D) OTHER INFORMATION:  /function= "deletes ScaI and PvuII
            site from prolylendopeptidase gene"
            /product= "synthetic oligonucleotide"

-continued (xi) SEQUENCE DESCRIPTION: SEQ ID NO:2:

GGGAGTAGGA GTTCTGGATA TGCTTCGTTA TAATAAGTTT ACTG                44

(2) INFORMATION FOR SEQ ID NO:3:

(i) SEQUENCE CHARACTERISTICS:
        (A) LENGTH:  54 base pairs
        (B) TYPE:  nucleic acid
        (C) STRANDEDNESS:  double
        (D) TOPOLOGY:  linear (ii) MOLECULE TYPE:  DNA (genomic)

(ix) FEATURE:
        (A) NAME/KEY:  misc_feature
        (B) LOCATION:  1..54
        (D) OTHER INFORMATION:  /function= "creates new EcoRI site
            in prolylendopeptidase gene"
            /product= "synthetic oligonucleotide"

(xi) SEQUENCE DESCRIPTION: SEQ ID NO:3:

AATTCATGAA GTACAACAAA CTTTCTGTGG CAGTTGCAGC CTTTGCTTTT GCAG         54

(2) INFORMATION FOR SEQ ID NO:4:

(i) SEQUENCE CHARACTERISTICS:
        (A) LENGTH:  23 base pairs
        (B) TYPE:  nucleic acid
        (C) STRANDEDNESS:  single
        (D) TOPOLOGY:  linear (ii) MOLECULE TYPE:  DNA (genomic)

(ix) FEATURE:
        (A) NAME/KEY:  misc_feature
        (B) LOCATION:  1..23
        (D) OTHER INFORMATION:  /function= "for preparation of
            oligonucleotide SEQ ID No 3"
            /product= "synthetic oligonucleotide U1"

(xi) SEQUENCE DESCRIPTION: SEQ ID NO:4:

AATTCATGAA GTACAACAAA CTT                                           23

(2) INFORMATION FOR SEQ ID NO:5:

(i) SEQUENCE CHARACTERISTICS:
        (A) LENGTH:  31 base pairs
        (B) TYPE:  nucleic acid
        (C) STRANDEDNESS:  single
        (D) TOPOLOGY:  linear (ii) MOLECULE TYPE:  DNA (genomic)

(ix) FEATURE:
        (A) NAME/KEY:  misc_feature
        (B) LOCATION:  1..31
        (D) OTHER INFORMATION:  /function= "for preparation of
            oligonucleotide SEQ ID No. 3"
            /product= "synthetic oligonucleotide U2"

(xi) SEQUENCE DESCRIPTION: SEQ ID NO:5:

TCTGTGGCAG TTGCAGCCTT TGCTTTTGCA G                                  31

(2) INFORMATION FOR SEQ ID NO:6:

(i) SEQUENCE CHARACTERISTICS:
        (A) LENGTH:  25 base pairs
        (B) TYPE:  nucleic acid
        (C) STRANDEDNESS:  single
        (D) TOPOLOGY:  linear (ii) MOLECULE TYPE: DNA (genomic)

(ix) FEATURE:
            (A) NAME/KEY: misc_feature
            (B) LOCATION: 1..25
            (D) OTHER INFORMATION: /function= "for preparation of
                oligonucleotide SEQ ID No. 3"
                /product= "synthetic oligonucleotide L1"

(xi) SEQUENCE DESCRIPTION: SEQ ID NO:6:

CACAGAAAGT TGTTGTACT TCATG                                                      25

(2) INFORMATION FOR SEQ ID NO:7:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 1..25
            (D) OTHER INFORMATION: /function= "for preparation of
                oligonucleotide SEQ ID No. 3"
                /product= "synthetic oligonucleotide L2"

(xi) SEQUENCE DESCRIPTION: SEQ ID NO:7:

CTGCAAAAGC AAAGGCTGCA ACTGC                                                     25

(2) INFORMATION FOR SEQ ID NO:8:

(i) SEQUENCE CHARACTERISTICS:
            (A) LENGTH: 686 amino acid residues
            (B) TYPE: amino acid
            (C) STRANDEDNESS: single
            (D) TOPOLOGY: linear (ii) MOLECULE TYPE: Protein (iv) ORIGINAL SOURCE:
            (A) ORGANISM: Flavobacterium meningosepticum (xi) SEQUENCE DESCRIPTION: SEQ ID NO:8:

Ala Gln Asn Ser Asn Val Leu Lys Tyr Pro Glu Thr Lys Lys Val Ser
 1               5                  10                  15

His Thr Asp Thr Tyr Phe Gly Thr Gln Val Ser Asp Pro Tyr Arg Trp
                20                  25                  30

Leu Glu Asp Asp Arg Ala Glu Asp Thr Lys Ala Trp Val Gln Gln Glu
            35                  40                  45

Val Lys Phe Thr Gln Asp Tyr Leu Ala Gln Ile Pro Phe Arg Asp Gln
    50                  55                  60

Leu Lys Lys Gln Leu Met Asp Ile Trp Asn Tyr Glu Lys Ile Ser Ala
65                  70                  75                  80

Pro Phe Lys Lys Gly Lys Tyr Thr Tyr Phe Ser Lys Asn Asp Gly Leu
                85                  90                  95

Gln Ala Gln Ser Val Leu Tyr Arg Lys Asp Ala Ala Gly Lys Thr Glu
            100                 105                 110

Val Phe Leu Asp Pro Asn Lys Phe Ser Glu Lys Gly Thr Thr Ser Leu
    115                 120                 125

Ala Ser Val Ser Phe Asn Lys Lys Gly Thr Leu Val Ala Tyr Ser Ile
130                 135                 140

Ser Glu Gly Gly Ser Asp Trp Asn Lys Ile Ile Ile Leu Asp Ala Glu

```
            145                 150                 155                 160
        Thr Lys Lys Gln Leu Asp Glu Thr Leu Leu Asp Val Lys Phe Ser Gly
                        165                 170                 175
        Ile Ser Trp Leu Gly Asp Glu Gly Phe Phe Tyr Ser Ser Tyr Asp Lys
                        180                 185                 190
        Pro Lys Glu Gly Ser Val Leu Ser Gly Met Thr Asp Lys His Lys Val
                        195                 200                 205
        Tyr Phe His Lys Leu Gly Thr Lys Gln Ser Gln Asp Glu Leu Ile Ile
                210                 215                 220
        Gly Gly Asp Lys Phe Pro Arg Arg Tyr Ile Gly Ala Tyr Val Thr Asp
        225                 230                 235                 240
        Asp Gln Arg Tyr Leu Val Val Ser Ala Ala Asn Ala Thr Asn Gly Asn
                        245                 250                 255
        Glu Leu Tyr Ile Lys Asp Leu Lys Asn Lys Thr Asp Phe Ile Pro Ile
                        260                 265                 270
        Ile Thr Gly Phe Asp Ser Asn Val Asn Val Ala Asp Thr Asp Gly Asp
                        275                 280                 285
        Thr Leu Tyr Leu Phe Thr Asp Lys Asp Ala Pro Asn Lys Arg Leu Val
                290                 295                 300
        Lys Thr Thr Ile Gln Asn Pro Lys Ala Glu Thr Trp Lys Asp Val Ile
        305                 310                 315                 320
        Ala Glu Thr Thr Glu Pro Phe Gln Ile Asn Thr Gly Gly Tyr Phe
                        325                 330                 335
        Phe Ala Thr Tyr Met Lys Asp Ala Ile Asp Gln Val Lys Gln Tyr Asp
                        340                 345                 350
        Lys Asn Gly Lys Leu Val Arg Ala Ile Lys Leu Pro Gly Ser Gly Asn
                        355                 360                 365
        Ala Ser Gly Phe Gly Gly Glu Lys Thr Glu Lys Asp Leu Tyr Tyr Ser
                        370                 375                 380
        Phe Thr Asn Tyr Ile Thr Pro Pro Thr Ile Phe Lys Tyr Asn Val Thr
        385                 390                 395                 400
        Thr Gly Asn Ser Glu Val Tyr Gln Lys Pro Lys Val Lys Phe Asn Pro
                        405                 410                 415
        Glu Asn Tyr Val Ser Glu Gln Val Phe Tyr Thr Ser Ser Asp Gly Thr
                        420                 425                 430
        Lys Ile Pro Met Met Ile Ser Tyr Lys Lys Gly Leu Lys Lys Asp Gly
                        435                 440                 445
        Lys Asn Pro Thr Ile Leu Tyr Ser Tyr Gly Gly Phe Asn Ile Ser Leu
                450                 455                 460
        Gln Pro Ala Phe Ser Val Val Asn Ala Ile Trp Met Glu Asn Gly Gly
        465                 470                 475                 480
        Ile Tyr Ala Val Pro Asn Ile Arg Gly Gly Glu Tyr Gly Lys Lys
                        485                 490                 495
        Trp His Asp Ala Gly Thr Lys Met Gln Lys Asn Val Phe Asn Asp
                        500                 505                 510
        Phe Ile Ala Ala Gly Glu Tyr Leu Gln Lys Asn Gly Tyr Thr Ser Lys
                        515                 520                 525
        Glu Tyr Met Ala Leu Ser Gly Arg Ser Asn Gly Gly Leu Leu Val Gly
                        530                 535                 540
        Ala Thr Met Thr Met Arg Pro Asp Leu Ala Lys Val Ala Phe Pro Gly
        545                 550                 555                 560
        Val Gly Val Leu Asp Met Leu Arg Tyr Asn Lys Phe Thr Ala Gly Ala
                        565                 570                 575
```

```
Gly Trp Ala Tyr Asp Tyr Gly Thr Ala Glu Asp Ser Lys Glu Met Phe
            580                 585                 590

Glu Tyr Leu Lys Ser Tyr Ser Pro Val His Asn Val Lys Ala Gly Thr
        595                 600                 605

Cys Tyr Pro Ser Thr Met Val Ile Thr Ser Asp His Asp Asp Arg Val
        610                 615                 620

Val Pro Ala His Ser Phe Lys Phe Gly Ser Glu Leu Gln Ala Lys Gln
625                 630                 635                 640

Ser Cys Lys Asn Pro Ile Leu Ile Arg Ile Glu Thr Asn Ala Gly His
                645                 650                 655

Gly Ala Gly Arg Ser Thr Glu Gln Val Val Ala Glu Asn Ala Asp Leu
                660                 665                 670

Leu Ser Phe Ala Leu Tyr Glu Met Gly Ile Lys Ser Leu Lys
                675                 680                 685

(2) INFORMATION FOR SEQ ID NO:9:

(i) SEQUENCE CHARACTERISTICS:
        (A) LENGTH: 19 amino acid residues
        (B) TYPE: amino acid
        (C) STRANDEDNESS: single
        (D) TOPOLOGY: linear (ii) MOLECULE TYPE: Protein (iv) ORIGINAL SOURCE:
        (A) ORGANISM: Flavobacterium meningosepticum (xi) SEQUENCE DESCRIPTION: SEQ ID NO:9:

Met Lys Tyr Asn Lys Leu Ser Val Ala Val Ala Ala Phe Ala Phe Ala
  1               5                  10                  15

Ala Val Ser
```